(12) United States Patent
Haase et al.

(10) Patent No.: US 12,351,712 B2
(45) Date of Patent: *Jul. 8, 2025

(54) BIJELS AND METHODS OF MAKING THE SAME

(71) Applicant: The Trustees of the University of Pennsylvania, Philadelphia, PA (US)

(72) Inventors: Martin F Haase, Philadelphia, PA (US); Daeyeon Lee, Wynnewood, PA (US); Kathleen J Stebe, Penn Valley, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 28 days.

This patent is subject to a terminal disclaimer.

(21) Appl. No.: 17/534,500

(22) Filed: Nov. 24, 2021

(65) Prior Publication Data

US 2022/0195171 A1   Jun. 23, 2022

Related U.S. Application Data

(63) Continuation of application No. 15/579,086, filed as application No. PCT/US2016/035031 on May 31, 2016, now Pat. No. 11,220,597.

(Continued)

(51) Int. Cl.
C08L 35/02     (2006.01)
A23P 30/00     (2016.01)
(Continued)

(52) U.S. Cl.
CPC .............. *C08L 35/02* (2013.01); *A23P 30/00* (2016.08); *A61K 8/25* (2013.01); *A61K 8/37* (2013.01); *A61K 8/8152* (2013.01); *A61L 27/025* (2013.01); *A61L 27/16* (2013.01); *A61L 27/56* (2013.01); *A61Q 19/00* (2013.01); *B01D 39/00* (2013.01); *B01J 14/00* (2013.01); *B01J 19/0093* (2013.01); *C08F 2/22* (2013.01);
(Continued)

(58) Field of Classification Search
None
See application file for complete search history.

(56) References Cited

U.S. PATENT DOCUMENTS 4,956,289 A      9/1990  Wrasidlo et al.
2002/0155208 A1  10/2002 Benjamins et al.
(Continued)

OTHER PUBLICATIONS

Haase et al., "Continuous Fabrication of Hierarchical and Asymmetric Bijel Microparticles, Fibers, and Membranes by Solvent Transfer-Induced Phase Separation (STRIPS)", Adv. Mater. 2015, 27, pp. 7065-7071 (Year: 2015).*

(Continued)

*Primary Examiner* — Kyung S Chang
(74) *Attorney, Agent, or Firm* — BakerHostetler

(57) ABSTRACT

A method of making a bijel includes dispersing surface-active nanoparticles in a ternary liquid mixture. The ternary liquid mixture includes a hydrophilic liquid, a hydrophobic liquid, and a solvent. The ternary liquid mixture is contacted with water. A bijel includes a stable mixture of two immiscible liquids separated by an interfacial layer of colloidal particles. The bijel has temperature-independent stability, and the domain sizes are below one micrometer.

19 Claims, 15 Drawing Sheets

Related U.S. Application Data

(60) Provisional application No. 62/169,295, filed on Jun. 1, 2015.

(51) Int. Cl.

| | | |
|---|---|---|
| *A61K 8/02* | (2006.01) | |
| *A61K 8/04* | (2006.01) | |
| *A61K 8/25* | (2006.01) | |
| *A61K 8/37* | (2006.01) | |
| *A61K 8/81* | (2006.01) | |
| *A61L 27/02* | (2006.01) | |
| *A61L 27/16* | (2006.01) | |
| *A61L 27/56* | (2006.01) | |
| *A61Q 19/00* | (2006.01) | |
| *B01D 39/00* | (2006.01) | |
| *B01J 14/00* | (2006.01) | |
| *B01J 19/00* | (2006.01) | |
| *C08F 2/22* | (2006.01) | |
| *C08F 2/44* | (2006.01) | |
| *C08F 2/50* | (2006.01) | |
| *C08F 8/12* | (2006.01) | |
| *C08F 8/44* | (2006.01) | |
| *C08F 120/18* | (2006.01) | |
| *C08F 122/10* | (2006.01) | |
| *C08J 5/18* | (2006.01) | |
| *C08L 33/08* | (2006.01) | |

(52) U.S. Cl.
CPC .............. *C08F 2/44* (2013.01); *C08F 2/50* (2013.01); *C08F 8/12* (2013.01); *C08F 8/44* (2013.01); *C08F 120/18* (2013.01); *C08F 122/1006* (2020.02); *C08J 5/18* (2013.01); *C08L 33/08* (2013.01); *A61K 8/0241* (2013.01); *A61K 8/027* (2013.01); *A61K 8/04* (2013.01); *A61K 2800/413* (2013.01); *A61K 2800/612* (2013.01); *B01D 2239/0258* (2013.01); *B01J 2219/00844* (2013.01); *C08J 2333/08* (2013.01); *C08J 2335/02* (2013.01); *C08L 2201/54* (2013.01); *C08L 2203/02* (2013.01); *C08L 2203/12* (2013.01); *C08L 2203/16* (2013.01); *C08L 2205/16* (2013.01)

(56) References Cited

U.S. PATENT DOCUMENTS

| | | |
|---|---|---|
| 2005/0064431 A1 | 3/2005 | Leon et al. |
| 2008/0125500 A1 | 5/2008 | Cates et al. |
| 2009/0130755 A1 | 5/2009 | Detamore et al. |
| 2010/0016200 A1 | 1/2010 | Nagare et al. |
| 2012/0071609 A1 | 3/2012 | Savla |
| 2013/0005945 A1 | 1/2013 | Yue et al. |
| 2015/0102265 A1 | 4/2015 | Russell et al. |
| 2018/0127577 A1 | 5/2018 | Haase et al. |

OTHER PUBLICATIONS

Sun et al., "Porous Polymer Catalysts with Hierarchical Structures," Chem. Soc. Rev., 2015, vol. 44, No. 17, pp. 6018-6034.
Tavacoli et al., "Novel, Robust, and Versatile Bijels of Nitromethane, Ethanediol, and Colloidal Silica: Capsules, Sub-Ten-Micrometer Domains, and Mechanical Properties," Adv. Funct. Mater, 2011, vol. 21, No. 11, pp. 2020-2027.
Crossley et al., "Solid Nanoparticles That Catalyze Biofuel Upgrade Reactions at the Water/Oil Interface," Science, 2010, vol. 327, No. 5961, pp. 68-72.
Haase et al., "Continuous Fabrication of Hierarchical and Asymmetric Bijel Microparticles, Fibers, and Membranes by Solvent Transfer-Induced Phase Separation (STRIPS)," Adv. Mater., 2015, vol. 27, No. 44, pp. 7065-7071.
Haase et al., "Development of Nanoparticle Stabilized Polymer Nanocontainers with High Content of the Encapsulated Active Agent and Their Application in Water-Borne Anticorrosive Coatings," Adv. Mater., 2012, vol. 24, No. 18, pp. 2429-2435.
Haase et al., "Tailoring of High-Order Multiple Emulsions by the Liquid-Liquid Phase Separation of Ternary Mixtures," Angew. Chem. Int. Ed., 2014, vol. 53, No. 44, pp. 11793-11797.
Lee et al., "Bicontinuous Macroporous Materials from Bijel Templates," Adv. Mater, 2010, vol. 22, No. 43, pp. 4836-4841.
Lee et al., "Hierarchically Porous Silver Monoliths from Colloidal Bicontinuous Interfacially Jammed Emulsion Gels," J. Am. Chem. Soc., 2011, No. 133, No. 18, pp. 6945-6947.
Parlett et al., "Hierarchical Porous Materials: Catalytic Applications," Chem. Soc. Rev., 2013, vol. 42, No. 9, pp. 3876-3893.
Vitantonio et al., "Robust Bijels for Reactive Separation via Silica-Reinforced Nanoparticle Layers," ACS Nano, 2019, vol. 13, No. 1, pp. 26-31.
Wang et al., "Co-continuous Composite Materials for Stiffness, Strength, and Energy Dissipation", Advanced Materials, 2011, 23, pp. 1524-1529.
White et al., "Influence of Particle Composition and Thermal Cycling on Bijel Formation," J. Phys.: Condens. Matter, 2008, vol. 20, No. 49, 494223.
Witt et al., "Bijel Reinforcement by Droplet Bridging: A Route to Bicontinuous Materials with Large Domains", Soft Matter, 2013, vol. 9, pp. 6773-6780.
Witt et al., "Microstructural Tunability of Co-Continuous Bijel-Derived Electrodes to Provide High Energy and Power Densities," J. Mater. Chem. A, 2016, vol. 4, No. 3, pp. 1000-1007.
Yow et al., "Formation of Liquid Core-polymer Shell Microcapsules", Soft Matter, 2006, vol. 2, pp. 940-949.
Yuan et al., "Insights into Hierarchically Meso-macroporous Structured Materials", J. Mater. Chem., 2006, vol. 16, pp. 663-677.
Zapata et al., "Hydrophobic Zeolites for Biofuel Upgrading Reactions at the Liquid-liquid interface in Water/oil Emulsions", J. Am. Chem. Soc., 2012, vol. 134, pp. 8570-8578.
Zhang et al., "Compartmentalized Droplets for Continuous Flow Liquid-Liquid Interface Catalysis," J. Am. Chem. Soc., 2016, vol. 138, No. 32, pp. 10173-10183.
Zhang et al., "Micrometer-Scale Mixing with Pickering Emulsions: Biphasic Reactions without Stirring," ChemSusChem., 2014, vol. 7, No. 2, pp. 391-396.
"Highlands and Drylands: Mountains, A Source of Resilience in Arid Regions", the Food and Agriculture Organization of the United Nations and Centre for Development and Environment of the University of Bern, 2001, 115 pages.
Aveyard et al., "Emulsions Stabilised Solely by Colloidal Particles," Advances in Colloid and Interface Science, 2003, pp. 100-102, 503-546.
Awala et al., "Template-free Nanosized Faujasite-type Zeolites", Nature Materials, vol. 14, Apr. 2015, pp. 447-451.
Bai et al., "Dynamics and Rheology of Nonpolar Bijels," Soft Matter, 2015, vol. 11, No. 26, pp. 5282-5293.
Berthiaum et al., "Tissue Engineering and Regenerative Medicine: History, Progress and Challenges", Annu. Rev. Chem, Biomol. Eng., 2011, vol. 2, pp. 403-430.
Boon et al., "Blue Energy from Ion Adsorption and Electrode Charging in Sea-and-River Water", 2011 Molecular Physics, vol. 109, 14 pages.
Bray A.J., "Theory of Phase Ordering Kinetics", Advances in Physics, vol. 51, 2008, 85 pages.
Brugger et al., "Microgels as Stimuli-Responsive Stabilizers for Emulsions", Langmuir, 2008, vol. 24, pp. 12202-12208.
Cai et al., "Bijels formed by direct mixing," Soft matter, 2017, vol. 13, No. 28, pp. 4824-4829.
Cates et al., "Bijels: A New Class of Soft Materials", Soft Matter, 2008, vol. 4, pp. 2132-2138.
Chai et al., "Ordered Porous Carbons with Tunable Pore Sizes as Catalyst Supports in Direct Methanol Fuel Cell", J. Phys. Chem. B, 2004, vol. 108, pp. 7074-7079.

(56) References Cited

OTHER PUBLICATIONS

Chen et al., "Multifunctionality of Three-dimensional Self-Assembled Composite Structure", Scripta Materials, 61, 2009, pp. 52-55.
Chevalier et al., "Emulsions Stabilized with Solid Nanoparticles: Pickering Emulsions," Colloids and Surfaces A: Physicochemical and Engineering Aspects, 2013, vol. 439, pp. 23-34.
Chung T., "Fabrication of Hollow-Fiber Membranes by Phase Inversion", Advanced Membrane Technology and Applications, 2008, pp. 821-839.
Destribat et al., "Emulsions Stabilized by Whey Protein Microgel Particles: Towards Food-trade Pickering Emulsions", Soft Mater, 2014, vol. 10, pp. 6941-6954.
Ding et al., "Metallic Mesoporous Nanocomposites for Electrocatalysis", J. Am. Chem. Soc., 2004, vol. 126, pp. 6876-6877.
Dong et al., "Bioinspired Electrospun Knotted Microfibers for Fog Harvesting", ChemPhysChem 2012, vol. 13, pp. 1153-1156.
Galiano et al., "UV-LED Induced Bicontinuous Microemulsions Polymerisation for Surface Modification of Commercial Membranes—Enhancing the Antifouling Properties," Separation and Purification Technology, 2018, vol. 194, pp. 149-160.
Greiner et al., "Electrospinning: A Fascinating Method for the Preparation of Ultrathin Fibers", Angew. Chem. Int. Ed., 2007, vol. 46, pp. 5670-5703.
Gubbels et al., Kinetic and Thermodynamic Control of the Selective Localization of Carbon Black at the Interface of Immiscible Polymer Blends, Chem. Mater., 1998, vol. 10, pp. 1227-1235.
Guillen et al., "Preparation and Characterization of Membranes Formed by Nonsolvent Induced Phase Separation: A Review", Industrial & Engineering Chemistry Research, 2011, vol. 50, pp. 3798-3817.
Haase et al., "Multifunctional Nanocomposite Hollow Fiber Membranes by Solvent Transfer Induced Phase Separation," Nat. Commun., 2017, vol. 8, No. 1, 1234.
Haase, MF et al., In Situ Mechanical Testing of Nanostructured Bijel Fibers, ACS Nano. May 31, 2016. vol. 10, No. 6; entire document.
Herzig et al., "Bicontinuous Emulsions Stabilized Solely by Colloidal Particles", Nature Materials, vol. 6, No. 12, 2007, pp. 966-971.
Hong et al., "Preparation, Bioactivity, and Drug Release of Hierarchical Nanoporous Bioactive Glass Ultrathin Fibers," Adv. Mater., 2010, vol. 22, No. 6, pp. 754-758.
Hu et al., "Hierarchical Structure of Electrospun Composite Fibers for Long-Term Controlled Drug Release Carriers," Advanced Healthcare Materials, 2012, vol. 1, No. 6, pp. 809-814.
Huang et al., "Bicontinuous structured liquids with sub-micro-metre domains using nanoparticle surfactants," Nature nanotechnology, 2017, vol. 12, No. 11, pp. 1060-1064.
International Preliminary Report on Patentability for International Application No. PCT/US2016/035031, dated Dec. 5, 2017, 9 pages.
International Search Report and Written Opinion for International Application No. PCT/US2016/035031, dated Oct. 6, 2016, 11 pages.
Jansen et al., "From Bijels to Pickering Emulsions: A Lattice Boltzmann Study," Phys. Rev., 2011, vol. E 83, No. 4, 046707.
Jones et al., "High-temperature Nanoporous Ceramic Monolith Prepared from a Polymeric Bicontinuous Microemulsion Template", J. Am. Chem. Soc., 2009, vol. 131, pp. 1676-1677.
Kargar et al., "Investigation into the Potential Ability of Pickering Emulsions (Food Grade Particles) to Enhance the Oxidative Stability of Oil-in-Water Emulsions", Journal of Colloid and Interface Science, vol. 366, (2012), pp. 209-215.
Klemm et al., "Fog as a Fresh-Water Resource: Overview and Perspectives", AMBIO, 2012, vol. 41, pp. 221-234.
Lai et al., "Profiting from Nature: Macroporous Copper with Superior Mechanical Properties", Chem. Communications, 2007, pp. 3547-3549.
Lee et al., "Developing Monolithic Nanoporous Gold with Hierarchical Bicontinuity Using Colloidal Bijels," J. Phys. Chem. Lett., 2014, vol. 5, No. 5, pp. 809-812.
Lee et al., Making a Robust interfacial Scaffold: Bijel Rheology and its Link to Processability, Advanced Functional Mater., 2013, vol. 23, pp. 417-423.
Martina et al., "Developing Macroporous Bicontinuous Materials as Scaffolds for Tissue Engineering",Biomaterials, vol. 26 (2005), pp. 5609-5616.
Marto et al., "Melatonin-Based Pickering Emulsion for Skin's Photoprotection," Drug Delivery, 2016, No. 23, No. 5, pp. 1594-1607.
McDevitt et al., "Improving Cyclability of ZnO Electrodes through Microstructural Design," ACS Appl. Energy Mater, 2019, No. 2, No. 11, pp. 8107-8117.
Moutos et al., "A Biomimetic Three-dimensional Woven Composite Scaffold for Functional Tissue Engineering of Cartilage", Nature Materials, vol. 6, Feb. 2007, pp. 162-167.
Sanz et al., "Colloidal Gels Assembled via a Temporary Interfacial Scaffold," Phys. Rev. Lett., 2009, vol. 103, No. 25, 255502.
Sepehri et al., "Nanostructured Materials for Hydrogen Storage", Advanced Materials Research, Bd., vol. 132, 2010, pp. 137-153.
Soares et al., "Electrical Conductivity in Carbon Black-loaded Polystyrene-polyisoprene Blends. Selective Localization of Carbon Black at the Interface", Polymer Bulletin, (1995), vol. 35, Iss, 1-2, pp. 223-228.
Song et al., "Monodisperse w/w/w/ Double Emulsion Induced by Phase Separation", Langmuir 2012, vol. 28, pp. 12054-12059.
Srivastava et al., "Mesoporous Materials with Zeolite Framework: Remarkable Effect of the Hierarchical Structure for Retardation of Catalyst Deactivation," Chem. Commun., 2006, No. 43, 4489.
Stratford et al., "Colloidal Jamming at Interfaces: A Route to Fluid-Bicontinuous Gels", Science, Sep. 30, 2005, vol. 309, pp. 2198-2202.
Studart et al., "Arrested Coalescence of Particle-Coated Droplets into Nonspherical Supracolloidal Structures," J. Phys. Chem. B, 2009, vol. 113, No. 12, pp. 3914-3919.
Tanaka et al., "Monolithic Silica cols. for High-efficiency Chromatographic Separations", Journal of Chromatography A., 965, (2002), pp. 35-49.
Tavacoli et al., "Bicontinuous Emulsions Stabilized by Colloidal Particles (Chapter 6)", Royal Society of Chemistry 2015, pp. 129-168.
Torquato et al., "Multifunctional Composites: Optimizing Microstructures for Simultaneous Transport of Heat and Electricity", Physical Review Letters, The American Physical Society, vol. 89, No. 26, Dec. 23, 2002—pp. 26601-01-266601-4.

* cited by examiner

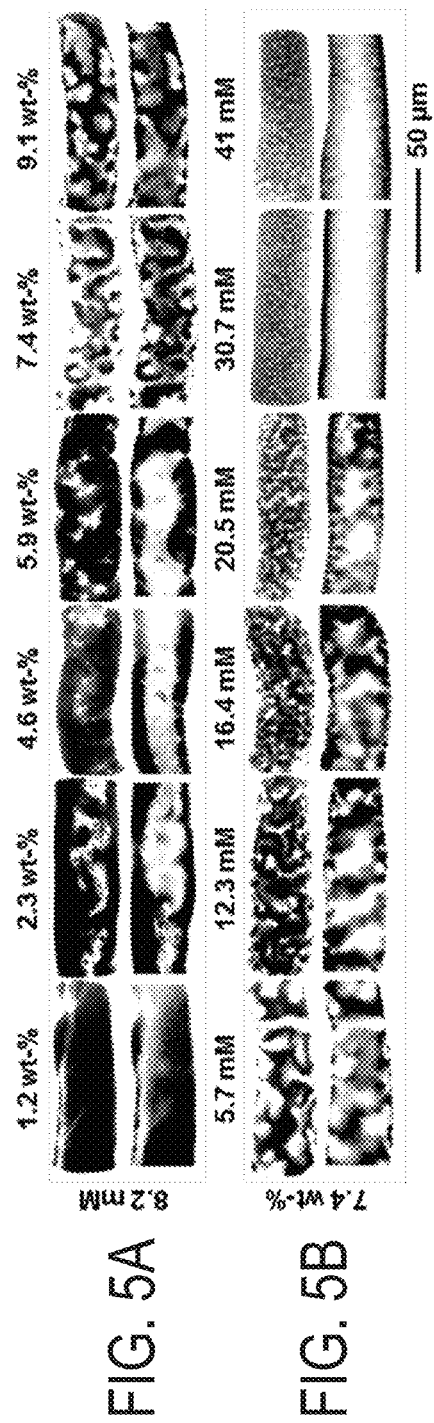

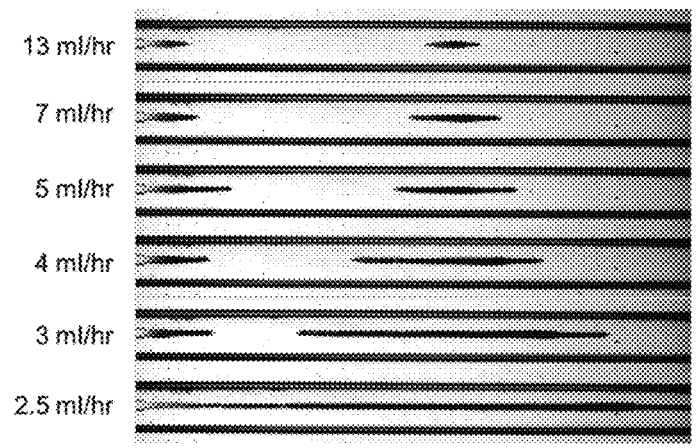 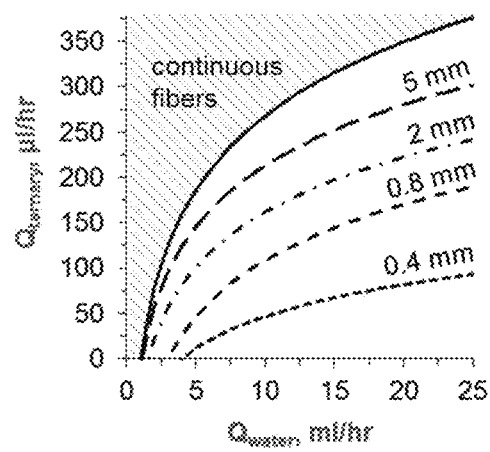
FIG. 9A                    FIG. 9B

500 μm

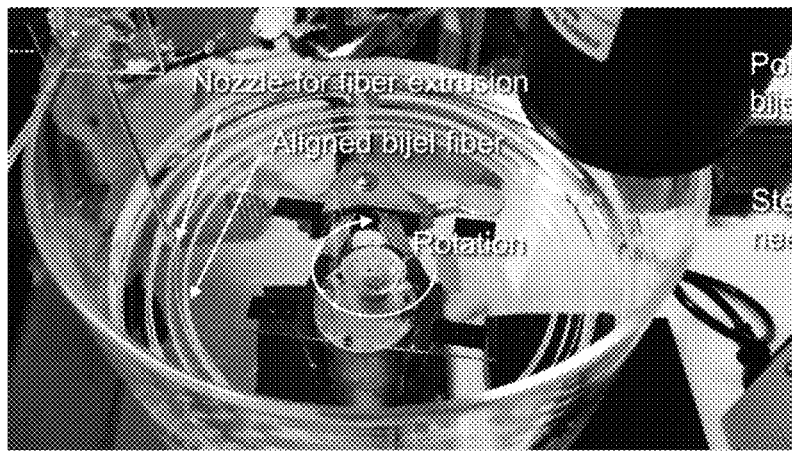 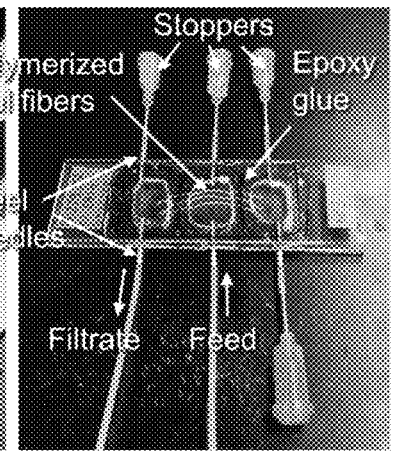
FIG. 11A                    FIG. 11B

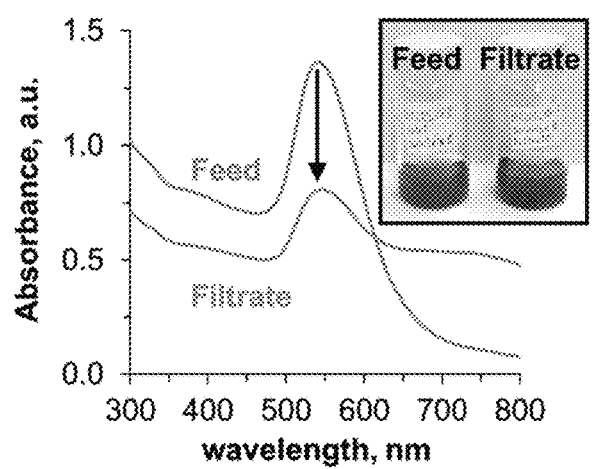
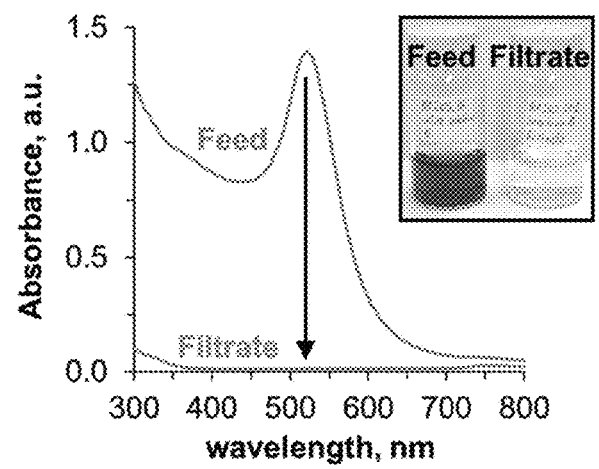
FIG. 13A
FIG. 13B

BIJELS AND METHODS OF MAKING THE SAME

CROSS REFERENCE TO RELATED APPLICATIONS

This application is a continuation of U.S. Non-Provisional application Ser. No. 15/579,086, entitled Bijels and Methods of Making the Same, filed Dec. 1, 2017, which is the U.S. phase of International Application No. PCT/US2016/035031, filed May 31, 2016, which claims priority to U.S. Provisional Application No. 62/169,295, filed Jun. 1, 2015. The disclosure of each of these applications are incorporated herein by reference in its entirety for any and all purposes.

FIELD OF THE INVENTION

The invention relates to bicontinuous interfacially jammed emulsions (bijels), and methods of making and using the same.

BACKGROUND OF THE INVENTION

Bicontinuous interfacially jammed emulsions (bijels) are soft materials with potential applications in areas including healthcare, cosmetics, food, energy and chemical technologies. However, currently their fabrication is limited to only a small number of immiscible liquid pairs. Moreover, bicontinuous domain sizes are still in the range of tens of micrometers and the fabrication is inefficient due to its batch-wise nature and expensive starting materials.

SUMMARY OF THE INVENTION

Embodiments of the present invention relate to methods of making a bijel. The methods include dispersing surface-active nanoparticles in a ternary liquid mixture, wherein the ternary liquid mixture includes a hydrophilic liquid, a hydrophobic liquid, and a solvent. The ternary liquid mixture is subsequently contacted with water, which induces a ternary phase separation initiated by mass transfer of the solvent (solvent transfer-induced phase separation, STRIPS). According to some embodiments, the methods can be altered or tuned to include any of a number of nanoparticles having diverse chemistries or different combinations of bicontinuous phases. Such embodiments may result in diverse chemical and physical properties of the resulting bijel, or may provide for bijels capable of varied applications, including applications such as facilitating catalysis, chemical reactions, or filtration/separation.

Another embodiment of the present invention relates to a bijel (e.g., a bijel fiber or a bijel membrane) comprising a stable bicontinuous mixture of two immiscible liquids separated by an interfacial layer of colloidal particles. The bijel has temperature-independent stability, and the domain sizes of the bijel are less than about 10 µm (e.g., they may range from about 100 nm to about 5 µm, or from about 200 nm to about 4 µm, or from about 300 nm to about 3 µm).

Additional embodiments of the present invention relate to materials and compositions comprising bijel fibers or bijel membranes of the present invention. Non-limiting examples of such materials and compositions include a fiber scaffold for tissue engineering (e.g., solid polymer scaffold), a cosmetic composition, a food composition, a filter, and a fog harvesting mesh. According to an additional embodiment, a cross-flow reactor may comprise bijels of the present invention. The bijels have potential applications in healthcare, cosmetics, food, energy and chemical technologies. Applications for the bijels in accordance with certain embodiments of the present invention include providing structural frameworks for chemical separations and catalytic processes.

BRIEF DESCRIPTION OF THE DRAWINGS

FIG. 3A provides 3D-reconstructions of fiber segments from confocal z-stacks and corresponding equatorial slices. Insets correspond to magnified sections of the fiber surface.

FIG. 3B depicts water fraction, surface pore size and surface area (measured from the micrographs in FIG. 3A by image analysis) of the fibers vs. silica and CTAB concentrations.

FIGS. 5A and 5B provide confocal scanning laser micrographs of liquid DEP in water fibers for different silica concentrations and a fixed CTAB concentration of 8.2 mM (upper two rows) and different CTAB concentrations and a fixed silica concentration of 7.4 wt-% (lower two rows). For one set of conditions, the first row corresponds to 3D top views of the fibers and the lower row to a slice of the equatorial position of the fiber.

FIG. 7A provides a photograph of aligned fibers connected to two DEP reservoirs (schematically drawn).

FIG. 7B provides a confocal scanning micrograph time series showing the coarsening of fibers at pH 3.

FIG. 7C provides a confocal scanning micrograph time series showing the stability of fibers at pH 9, the diffusion of a hydrophobic fluorescent dye throughout the fibers and the diffusion of a hydrophilic dye into the fibers.

FIGS. 9A and 9B illustrate bijel fiber length dependence on the flow rates in the microfluidic system, in accordance with embodiments of the present invention.

FIGS. 9A and 9B depict micrographs of bijel fiber segments just after pinch-off from the glass capillary tip flowing in the continuous water phase channel, wherein the segments have been formed at varying continuous water flow rates (2.5 ml/hr-13 ml/hr) for a constant ternary flow rate of 50 μl/hr.

FIG. 9B shows the preferred ternary and continuous water flow rates to form fiber segments of specified length (0.4 mm to 5 mm). The top line represents the transition from fiber segments to continuous fibers.

FIG. 10A depicts a membrane formed on a glass substrate.

FIG. 10B depicts a membrane formed on a polystyrene substrate.

FIG. 11A depicts an apparatus designed to collect STRIPS bijel fibers as aligned bundles within a water-filled collection container.

FIG. 11B depicts a device configured to test the separation selectivity and flux properties of silica stabilized poly(HDA) bijel fiber membrane walls.

FIG. 13A depicts separation of monodisperse gold nanoparticles having diameters of 100 nm from water using STRIPS bijel membranes. The 100 nm gold nanoparticles are fluxed through silica-stabilized poly(HDA) bijel fibers produced using 7.2 vol-% silica nanoparticles in the ternary liquid mixture.

FIG. 13B depicts separation of monodisperse gold nanoparticles having diameters of 15 nm from water using STRIPS bijel membranes. The 15 nm gold nanoparticles are fluxed through silica-stabilized poly(HDA) bijel fibers produced using 12.7 vol-% silica nanoparticles in the ternary liquid mixture.

DETAILED DESCRIPTION OF THE INVENTION

Figure 1A:
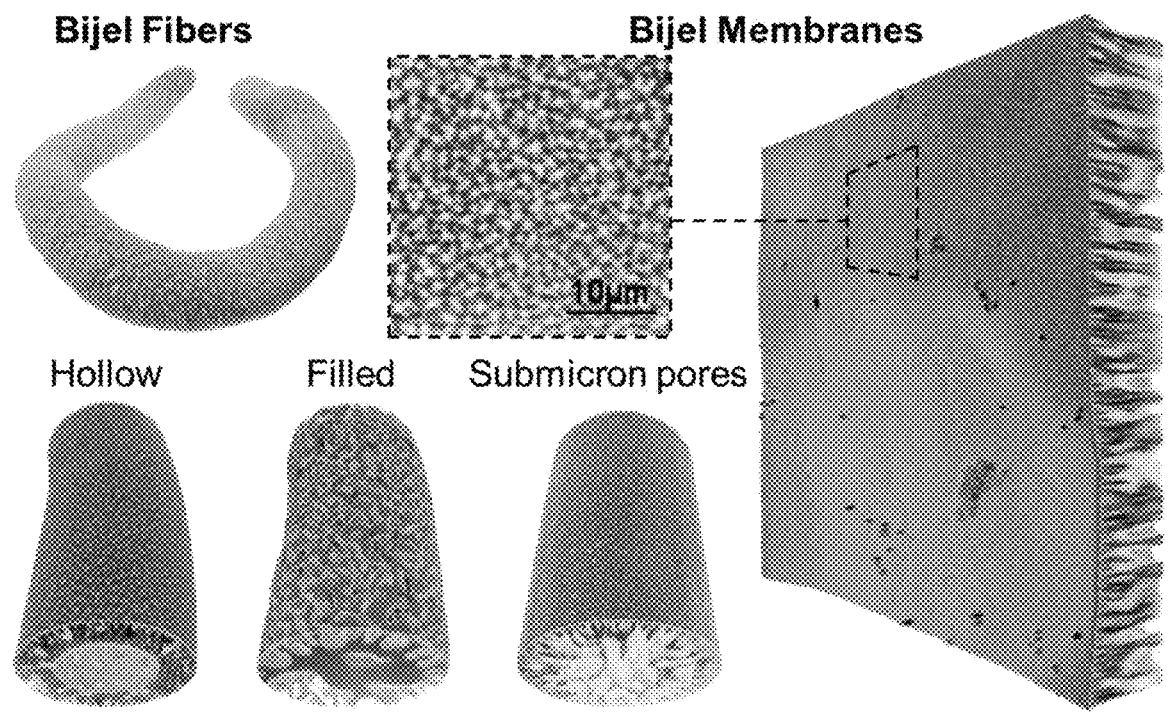
FIG. 1A provides 3D reconstructions of confocal scanning laser micrographs of liquid bijel fibers and membranes according to embodiments of the present invention.

The inventors have developed new methods for producing particle stabilized emulsions referred to as "bijel materials" or "bijels." In particular, the inventors have discovered that bijels can be manufactured continuously in more cost-effective and efficient ways, that have greater stability across a range of temperatures, and that can be tailored to various end uses.

As used herein, a bijel includes a bicontinuous interfacially jammed emulsion gel, which are nonequilibrium structures formed by jamming colloidal particles at the interface between two partially miscible fluids undergoing spinodal decomposition. In contrast to conventional emulsions, bijels have a stable bicontinuous liquid architecture composed of two immiscible liquids separated by an interfacial layer of jammed colloidal particles. The bicontinuous structure may be accessible via the mechanism of spinodal decomposition. Spinodally decomposing liquid-liquid mixtures are dynamically evolving nonequilibrium structures, which can yield two completely separated phases. Spinodal decomposition can be arrested during phase separation by solidification of one of the phases. This approach has been established for the formation of phase inversion membranes or electrospun fibers. In both cases, the rapid removal of the solvent causes the solidification of a phase-separating polymer.

Previous "heat transfer" methods involved dispersing particles in a mixture of two immiscible solvents at a temperature that was high enough for the solvents to be miscible, and subsequently quenching the temperature of the mixture (i.e., quickly cooling the mixture), thereby causing the fluids to separate via spinodal decomposition. In accordance with these methods, bicontinuous domain sizes were in the range of tens of micrometers and the fabrication was inefficient due to its batch-wise nature and expensive starting materials.

The inventors surprisingly developed bijels that can be manufactured continuously in more cost-effective and efficient ways, that have greater stability across a range of temperatures, and that can be tailored to various end uses. Embodiments of the present invention relate to the formation of bijel materials by solvent transfer induced phase separation (STRIPS). In accordance with these embodiments, a solvent (e.g., ethanol) acts as a miscibility mediator for a hydrophilic liquid (e.g., water) and a hydrophobic liquid (e.g., oil); and bijels are formed by introducing surface active nanoparticles to the ternary mixture.

Embodiments of the bijel manufacturing described herein have significant potential for large-scale manufacturing of hierarchically structured bijels for applications that require bicontinuous liquid structures, such as drug delivery, interfacial catalysis, edible bijels and liquid-liquid extraction. According to one embodiment, a method of making a bijel includes dispersing surface-active nanoparticles in a ternary liquid mixture (i.e., a mixture comprising three different liquids), wherein the ternary liquid mixture comprises a hydrophilic liquid (e.g., water, ethylene glycol, ethanediol), a hydrophobic liquid (e.g., an oil such as diethyl phthalate (DEP), dimethylphthalate, 1,6-hexanediol diacrylate, 1,6-diacetoxyhexane, trimethylolpropane triacrylate, dipentaerythritol pentaacrylate, laurylacrylate, butylacrylate, oleic acid, chloroform, styrene, triacetin, decanol, toluene, etc.), and a solvent (e.g., methanol, ethanol, propanol, acetic acid, dimethylsulfoxide, acetone, tetrahydrofuran etc.); and subsequently contacting the mixture with water. Following contact with water, mass transfer of the solvent initiates ternary liquid-liquid phase separation. Thus, a ternary phase separation induced by mass transfer of the solvent (STRIPS-process) serves as the basis for the bijel structure. The method may further comprise a step of mixing the hydrophilic liquid, the hydrophobic liquid and the solvent to form the initial ternary liquid mixture.

Unlike previous methods, embodiments of the present invention do not require changes in temperature to initiate phase separation. According to preferred embodiments, the method does not involve changing the temperature of the ternary liquid mixture either before or after the surface-active nanoparticles are dispersed in the mixture. According to particular embodiments, the method of making a bijel may be performed at room temperature (e.g., about 23° C. to about 26° C.). The use of commercially available silica and ionic surfactants enable the method to be less expensive than prior art systems.

Figure 2A:
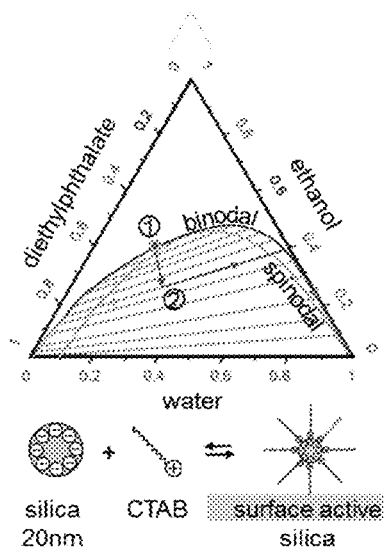
FIG. 2A provides a liquid-liquid equilibrium phase diagram of an embodiment of a ternary system comprising DEP, ethanol and water (volume fractions). Lines with arrows depict the estimated compositional trajectory of a ternary liquid volume undergoing phase separation as a consequence of ethanol and water loss. Below the phase diagram, the surface modification of silica nanoparticles by CTAB is depicted schematically.

As used herein, surface-active nanoparticles are nanoparticles (e.g., silica nanoparticles) that have been treated with an oppositely-charged ionic surfactant, whereby the surfactant imparts surface activity to the nanoparticles by interacting electrostatically with the surface of the nanoparticles (see, e.g., FIG. 2A). This is contrary to colloidal silica used in prior art bijel systems, whereby the silica particles are chemically modified (e.g., by silanization). Embodiments of the present invention comprise mixing the nanoparticles with the ionic surfactant to provide the surface-active nanoparticles.

For particle-stabilized emulsions, the wetting of the immiscible fluids on the surface of the particles determines the emulsion type. Particles wetted more by the oil phase stabilize water in oil droplets, while particles wetted more by the water phase stabilize oil in water droplets. To stabilize bijels, it is preferable to tune the surface chemistry of the particles in a way that both fluids, oil and water, wet the surface equally well. Neutral wetting renders bijel formation challenging because the extent of the chemical surface modification has to be precisely adjusted for any pair of immiscible liquids. Prior art systems typically require a process of tuning the particle surface chemistry to facilitate neutral wetting. The interfacially jammed particle layer in most prior art systems comprises colloidal silica synthesized by the Stoeber method. Chemical surface modifications such as silanization make these particles interfacially active.

In the first bijel system composed of the partially immiscible liquids water and 2,6 lutidine, the researchers synthesized 3-(aminopropyl)triethoxysilane modified Stoeber particles for the bijel stabilization (Herzig, E. M., et al. "Bicontinuous emulsions stabilized solely by colloidal particles." Nature materials 6.12 (2007): 966-971). To allow for the neutral wetting of the particles, it was necessary to dry the particles at 170° C. for a specified amount of time. This specific surface modification is only applicable to the water-lutidine system since the lutidine molecules are necessary to achieve the near neutral wetting conditions.

Another known method of surface modification of Stoeber-silica particles is carried out by chemically reacting hexamethyldisilazane with the silanol groups on the silica surface (Tavacoli, Joe W., et al. "Novel, Robust, and Versatile Bijels of Nitromethane, Ethanediol, and Colloidal Silica: Capsules, Sub-Ten-Micrometer Domains, and Mechanical Properties." Advanced Functional Materials 21.11 (2011): 2020-2027). The method is applied for the immiscible liquid system composed of ethanediol/nitromethane. The amount of hexamethyldisilazane added to the reaction mixture determines the extent of the chemical surface modification and can be adjusted to control the wetting properties. After the reaction, subsequent cycles of centrifugation, decantation and redispersion are required to remove unreacted synthesis components.

In accordance with embodiments of the present invention, commercially available silica nanoparticles may be employed for the bijel stabilization. Instead of chemically treating the nanoparticles (as described above with respect to prior art systems), oppositely charged surfactants are added together with the bare particles to the ternary liquid mixture. The surfactants fulfill two tasks: (i) disperse the particles in the ternary mixture and (ii) impart the surface activity to the particles. Compared to previous studies, embodiments of the present invention demonstrate that the utilization of ionic surfactants enables a straightforward surface modification that does not require careful tuning of the particle surface chemistry to facilitate neutral wetting. This strategy not only facilitates the bijel formation, but makes it highly cost effective and allows for the use of significantly smaller particles and higher particle quantities. Moreover, it allows the utilization of a large variety of different colloidal materials for the stabilization of bijels formed by the STRIPS process. Such colloidal materials include different ceramic particles ($Al_2O_3$, SiN, $TiO_2$), hydrogel particles (polyacrylic acid, Poly(N-isopropylacrylamide), polyallylamine hydrochloride), catalytic particles (zeolithe, silver or $TiO_2$ particles). Generally it is believed that the charged surface groups of these materials serve as adsorption sites for oppositely charged surfactants, which introduce the partial hydrophobicity to the particles and thereby the bijel stabilization capability.

Furthermore, tuning the concentration of the ionic surfactants enables the formation of a variety of different bijel architectures, as described herein.

To obtain nanoparticles that are dispersible in the ternary mixture and that efficiently stabilize the bijel structure, it is preferable to adjust the number of adsorption sites for the ionic surfactants on the nanoparticle surface. According to particular embodiments, adsorption sites on the surface of silica particles are dissociated silanol groups. The number of dissociated silanol groups determines the amount of adsorbed ionic surfactants. When the amount of adsorbed surfactants is either too high or too low, the nanoparticle dispersibility in the ternary mixture and the bijel stabilization capability may be compromised. The number of dissociated silanol groups can be regulated by the pH value. Above pH values of 6, the number of silanol groups grows strongly. According to particular embodiments, aqueous silica particles above a pH value of 6 cannot be dispersed in the ternary mixture irrespective of the cetyltrimethylammonium bromide (CTAB) concentration, most likely due to excessive CTAB adsorption. For acidic pH values (pH<5) the amount of negatively charged silanol groups is comparably small and does not change significantly. According to particular embodiments, lowering the pH below 5 facilitates the silica dispersibility in ternary mixtures for CTAB concentrations above 10 mM when DEP is the oil, and above 18 mM when HDA is the oil. Thus, a reduced number of adsorption sites are favorable for the particle dispersibility, according to some embodiments.

According to one embodiment, (3-amino-propyl) trimethoxysilane modified Ludox particles were employed to form bijel fibers and membranes, instead of bare silica particles. The chemical modification with (3-amino-propyl) trimethoxysilane was carried out in a flask with 20 vol-% acetic acid, 30 vol-% water, 30 vol-% ethanol and 20 vol-% Ludox TMA suspension under heating at 80° C. for 12 hours in a stirred round flask. The volume of (3-amino-propyl) trimethoxysilane added to this mixture was varied, in order to vary the number of amino functionalized surface groups on the nanoparticles. After the synthesis, the ethanol was evaporated and the particles were centrifuged, redispersed in pure water and dialyzed for 24 hours. The functionalized and washed particles were dispersed in the ternary mixture with the anionic surfactant docusate sodium salt (AOT) at a concentration of 10 mM at pH 3. The negatively charged sulfate group of AOT adsorbed electrostatically on the positively charged amino groups on the nanoparticles. According to particular embodiments, only when the (3-amino-propyl) trimethoxysilane volume fraction during the synthesis was below 1.2%, the particles can be dispersed in the ternary mixture with AOT; whereas above 1.2 vol-% (3-amino-propyl) trimethoxysilane, the particles aggregate, most likely due to high aminosilane coverage on the surface and consequently high amounts of adsorbed AOT molecules.

According to particular embodiments, the concentration of the surfactant (e.g., CTAB or AOT) added to the ternary liquid mixture is between about 10 mM and about 120 mM (with the total ternary volume as the reference).

According to particular embodiments, the nanoparticle (e.g., silica) concentration is between about 5 wt % and about 25 wt % based on the total weight of all components in the ternary mixture. According to particular embodiments, adjusting the nanoparticle and surfactant concentration affects the bijel fiber and membrane morphology, whether or not a water channel forms through the center of the bijel fiber, and also affects the surface area of the bijels, as well as the surface pore size of the fibers as described in the examples below.

According to particular embodiments, the water is present in the ternary liquid mixture in an amount of about 10% to about 25% by total volume. The amount of water is adjusted to obtain a composition that is close to the critical point in the ternary phase diagram of the specific water/oil/solvent combination.

According to particular embodiments, the oil is present in the ternary liquid mixture in an amount of about 30% to about 50% by total volume. According to particular embodiments, the solvent (e.g., ethanol, acetic acid, DMSO or acetone) is present in the ternary liquid mixture in an amount of about 30% to about 50% by total volume. The concentration of ethanol in the ternary mixture is preferably adjusted to ensure miscibility of water and oil.

According to particular embodiments, the continuous water phase has a pH value of 3 to 5 and contains a concentration of 1 mM CTAB.

According to particular embodiments, the addition of solvent to the continuous water phase can be conducted in a range from 0% to 20% by volume of the total continuous phase. According to particular embodiments, adjusting the ethanol concentration in the continuous phase affects the porous structure of the bijels, as described in the examples below. The hydrophobic liquid in the ternary liquid mixture (also referred to as an "oil") may comprise one or more of a polymerizable monomer and an unpolymerizable oil.

Where a polymerizable monomer is employed, the monomer may be crosslinkable via radical polymerization in the presence of a photoinitiator. Non-limiting examples of polymerizable monomers that may be used in accordance with embodiments of the present invention include 1,6-hexanediol diacrylate, butylacrylate, laurylacrylate, styrene, trimethylolpropane triacrylate, or dipentaerythritol pentaacrylate. The monomers are preferably polymerizable upon exposure to UV light.

According to particular embodiments, the hydrophilic liquid of the ternary liquid mixture may be limited to a simple liquid which is polymerizable or non-polymerizable (e.g., water, polyethyleneglycoldiacrylate, acrylic acid, etc.). In other embodiments, the hydrophilic liquid includes the combination of a simple liquid and a substantially hydrophilic monomer which is polymerizable. The hydrophilic monomer can be polymerized to form a hydrogel in the aqueous/hydrophilic domains. Non-limiting examples of hydrophilic polymerizable monomers that may be used in accordance with embodiments of the present invention include polyethyleneglycol diacrylate (PEG-DA), acrylamide (5-% PEG-DA) or acrylic acid (5% PEG-DA). For example, a hydrophilic polymerizable monomer (e.g., PEG-DA) may be added to the hydrophilic liquid of the ternary mixture.

Additionally, a photoinitiator (e.g., Irgacure 2595) or a thermal initiator (e.g., potassium persulfate) may be added to the hydrophilic liquid of the ternary mixture with a fraction of approximately 1% (e.g., from 0.50% to 1.50%). After the bijel is formed, polymerization of the hydrophilic monomer may be initiated by UV-light radiation or heat exposure (e.g., 70° C.), respectively.

According to some embodiments, the bijels are "polymerized" (e.g., the monomers of the oil phase are polymerized and/or the hydrophilic monomers present in the hydrophobic liquid/water phase are polymerized). According to other embodiments, the bijels are not polymerized. When the bijels are not polymerized, the only solid components of the bijels are the nanoparticles located at the oil-water interface, and the remainder of the bijels is liquid.

Some of the advantages of STRIPS that is used in accordance with embodiments of the present invention are described below.
  (i) Large varieties of liquid combinations are possible; in ternary systems, water can be mixed with a larger variety of apolar liquids than in binary systems.
  (ii) The ternary approach results in bijel materials with temperature-independent stability. This means that the bijels are stable at a wide range of temperatures, such as 5° C. to 90° C. A "stable" bijel refers to no remixing of water and oil as well as no coarsening of the bicontinuous domains. In particular, these features makes bijels more suitable as biphasic chemical reaction media.
  (iii) The fast quenching of STRIPS allows for the formation of bijel domain sizes below one micrometer. The pore diameter sizes of bijel membranes in accordance with embodiments of the present invention may range between about 5 nm and about 10,000 nm. In contrast, typical domain sizes of prior art bijels were above ten micrometers.
  (iv) Bijels formed upon STRIPS can be produced continuously as fibers or planar membranes. On the other hand, binary liquid mixture templated bijels are typically formed during batch processes in thin cuvettes.

(v) The bijel fibers can be 2D or 3D-printed to obtain a controlled complex fiber assembly for desired applications. In accordance with some embodiments of the present invention, bijel fibers may have diameters between about 1 μm and about 2000 μm.

Embodiments of the methods of the present invention enable the formation of at least three different types of bijel materials by STRIPS, namely: (1) bijel fibers (e.g., by using microfluidics to flow the ternary liquid mixture into a water channel), (2) bijel fiber segments or microparticles and (3) bijel membranes (e.g., by immersing a flat substrate coated with a thin film of the ternary liquid mixture into a water bath). With reference to FIG. 1A, the 3D reconstruction on the upper left corner shows a curved section of a porous fiber. Below, three examples of possible fiber morphologies are shown. The isometric perspectives of fiber segments show the surface morphology and the vertical cross section of the fibers. It is possible to fabricate hollow fibers with a porous shell composed of a bicontinuous water/oil scaffold and a continuous water channel in the center. Alternatively, the porous oil/water scaffold can be extended over the entire fiber volume. By controlling the conditions, partially-filled fibers with submicron sized surface and internal pores can be obtained. Also shown in FIG. 1A is a 3D reconstruction of an embodiment of a planar bijel membrane with a magnified section of the surface. The membranes have similar architectures as the fibers with small surface pores and a macroporous scaffold underneath.

In order to form bijel fibers, embodiments of the present invention comprise dispersing the surface-active nanoparticles in the ternary liquid mixture and subsequently injecting a stream of the mixture into water. This may be carried out by extruding the ternary liquid mixture through a dispensing needle (plastic or metal, 14-34 gauge) or glass tubing (0.02 mm-2 mm diameter) immersed in a water bath or located above a water bath with an air gap distance of 2 mm to 20 mm between outlet tip and water surface. When the extrusion is carried out with the outlet immersed in the water bath, it is preferable to coat the needle or glass tubing with the cationic polyelectrolyte polydiallyldimethylammonium chloride (polyDADMAC). The polymer coating prevents the adhesion of the fiber constituents to the capillary tip and enables a uniformly outflowing liquid fiber. The coating is carried out by immersing the needle for thirty seconds into a water bath with 0.1 wt-% polyDADMAC and 500 mM NaCl. Subsequently the needle needs to be rinsed with pure water and dried.

In the examples provided herein, bijel fibers were prepared by contacting the ternary liquid mixture with the water via glass capillary based microfluidics. However, it is not necessary to utilize glass capillary based microfluidics, as any "nozzle" that will eject a stream of the ternary phase into an aqueous phase would be suitable for forming bijel fibers, in accordance with embodiments of the present invention.

Figure 2D:
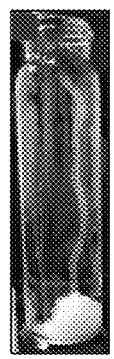
FIG. 2D provides photographs of a collection of fibers flowing out of a microfluidic device into a collection vial.
Figure 3A:
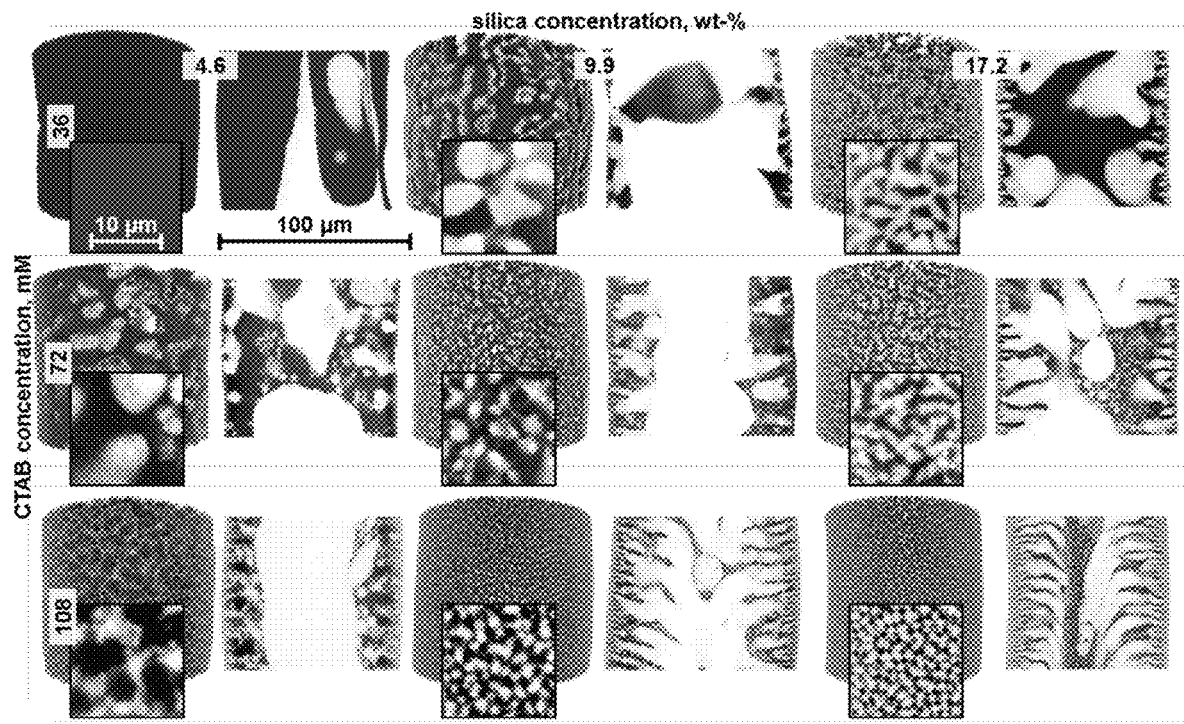
FIGS. 3A and 3B depict fiber surface and inner structure dependence on the silica and CTAB concentrations, in accordance with embodiments of the present invention.
Figure 4:
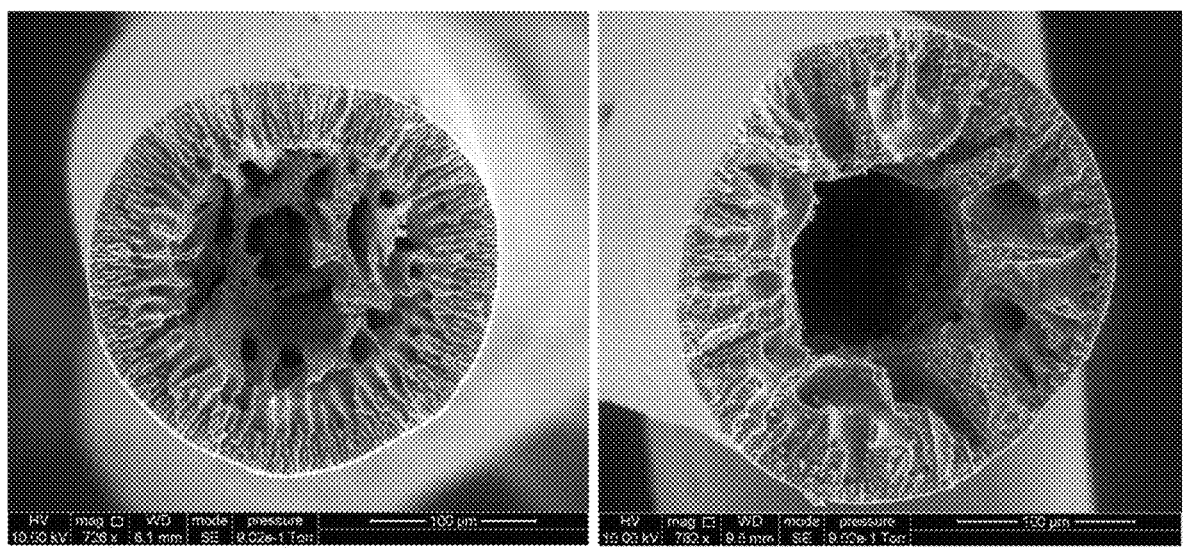
FIG. 4 provides cross-sectional views of poly-HDA fibers fabricated by polymerizing STRIPS bijel fibers.

A bijel fiber comprises a bijel in the form of an elongate strand or thread. For example, FIG. 2D shows fibers flowing out of a microfluidic device into a collection vial (the fiber began undulating after it exited the microfluidic device, which caused the fiber to spiral and then sink to the bottom of the collection vial). According to some embodiments, the bijel fiber has an internal "core" of water running through the length of the fiber, i.e., the bijel fiber has a core-shell structure wherein a continuous water channel extends lengthwise through the center of the fiber (see, e.g., FIG. 1A; FIG. 3A at 72 mM CTAB and 9.9 wt-% silica or 108 mM CTAB and 4.6 wt-% silica; FIG. 4 (right side) and FIG. 6B at 5% ethanol). According to alternative embodiments, the bijel fiber does not have a water core (i.e., the bijel fiber has a continuous structure). The presence or absence of the water channel can be controlled by adjusting one or more parameters selected from surfactant concentration, nanoparticle concentration and solvent concentration in the continuous phase, as described herein.

In order to form bijel membranes (i.e., bijels that are in the form of a substantially flat, planar membrane), embodiments of the present invention comprise dispersing the surface-active nanoparticles in the ternary liquid mixture, coating a thin film of the mixture onto a flat substrate (e.g., glass or polystyrene) and subsequently immersing the coated substrate in water, as described herein.

Embodiments of the present invention provide bijels made in accordance with the methods described herein. According to particular embodiments, a bijel comprises a stable mixture of two immiscible liquids separated by an interfacial layer of colloidal particles, wherein the bijel has temperature-independent stability, and wherein at least some of the domain sizes are below one micrometer.

According to particular embodiments, bijels of the present invention comprise numerous channels and pores. This sponge-like internal architecture can be on the nanometer scale (i.e., domain sizes of less than one micrometer), allowing for high surface areas of between about 1 $m^2/g$ and about 30 $m^2/g$.

According to particular embodiments, the diameters of the bijel fibers are between about 1 μm and about 2000 μm. According to alternative embodiments, the diameters of the bijel fibers are between about 1 μm and about 500 μm, or between about 1 μm and about 350 μm, or between about 1 μm and about 250 μm, or between about 1 μm and about 100 μm, or between about 10 μm and about 2000 μm.

According to the particular embodiments, the flow rates for the formation of bijel fibers can be adjusted to control the length of the bijel fibers. For bijel fibers formed with a 0.05 mm nozzle in a 0.3 mm channel, the continuous water flow rate is preferably between 1 ml/hr to 30 ml/hr and the flow rate of the ternary mixture preferably between 0.01 and 1.0 ml/hr. The resulting fiber length is preferably from 0.3 mm up to continuous fibers. The lengths of the bijel fibers can vary greatly, for example, between about 0.4 mm to about 1 meter. The bijel fibers may have any length, for example, at least about 1 meter, or at least about 5 meters, or at least about 10 meters, etc.

Preferably, the domains of the bijel fibers (i.e., the water-filled pores of the fibers) have diameters less than 50 micrometer; for example, between 50 micrometer and 1 micrometer, or between 50 micrometer and 10 micrometer, or between 20 micrometer and 1 micrometer, or between 10 micrometer and 1 micrometer, or between 10 micrometer and 500 nm, or between 5 micrometer and 1 micrometer, or between 2 micrometer and 500 nm, or between 1 micrometer and 500 nm, or between 1 micrometer and 300 nm.

The bijel fibers and membranes may have uniform surface pores with sizes ranging from 10 μm (10,000 nm) down to 5 nm. For example, the pores can range from 10 μm to 2 μm, from 2.5 μm to 1.5 μm, from 4 μm to 1.5 μm, from 1.5 μm to 0.8 μm, from 1 μm to 600 nm, from 700 nm to 400 nm, or from 400 nm to 5 nm.

The surface of the fibers and membranes can be covered by a densely packed layer of 20 nm silica colloids. It is possible to control the presence/absence of this packed nanoparticle film. When the nanoparticle film is present, the surface pores preferably become equal to the gaps between the densely packed nanoparticles, e.g., 5-15 nanometers. The densely packed silica nanoparticle film on the surface extends the application possibilities for the fibers/membranes for filtrations of particles/molecules of smaller sizes.

Figure 1B:
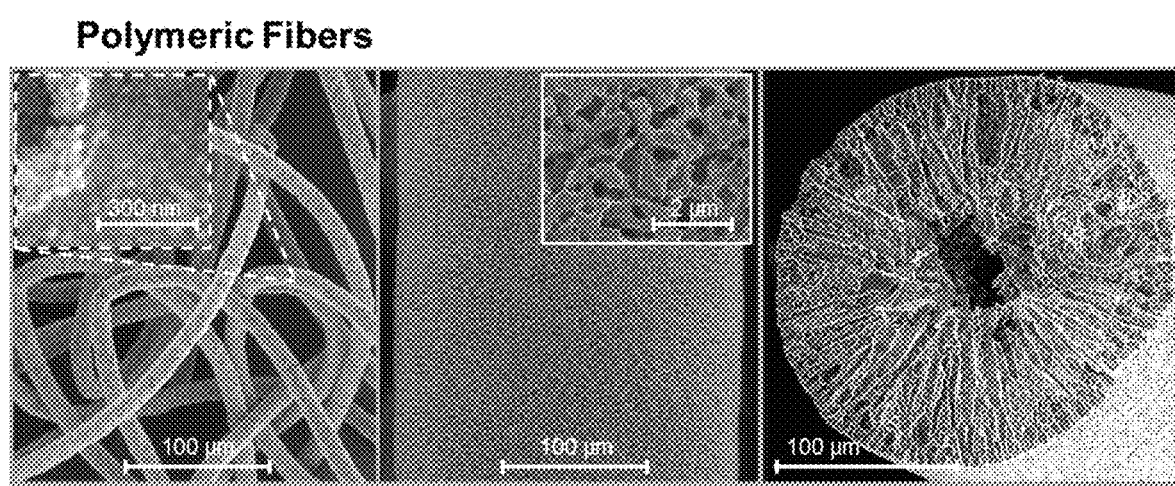
FIG. 1B provides electron micrographs of embodiments of polymerized nanoparticle stabilized bijel fibers. Left: fibers with 10 micrometer diameter, inset: magnification of fiber surface showing jammed nanoparticle film. Middle: a section of a fiber with 250 micrometer diameter, inset: bicontinuous surface morphology of a fiber. Right: cross sectional view of a 200 µm fiber.

FIG. 1B provides electron micrographs of bijel fibers that have been solidified by polymerization. The fiber surface is typically very porous and uniform (see, e.g., FIG. 1B) with interfacially jammed silica nanoparticles visible on the surface of the fibers. The surface morphology shows bicontinuous features and has domain sizes of micron and submicron dimensions. To the right of FIG. 1 a cross-sectional view of an embodiment of one of the larger specimens is shown. It can be seen that the fiber in this embodiment has hierarchical features; for example, a microporous skin and an interior infiltrated by micro- and radially aligned macropores can often be observed. This architecture is similar to phase inversion fibers and membranes. However, in contrast to a phase inversion fiber, bijel fibers of the present invention do not need a bore fluid to form a continuous water channel (or "core"), as the water channel may result naturally from the STRIPS process (among other differences).

According to particular embodiments, a bijel of the present invention can be used as a counter flow reactor for biphasic chemical reactions. Catalytic particle stabilized emulsion droplets for biphasic chemical reactions have previously been developed. Introducing bijel fibers of the present invention for this purpose could greatly improve the efficiency of the process: the porous structure of the fibers provides not only a larger surface area for the chemical reactions compared to the surface area of mere droplets, but the entire operation becomes a continuous process when the bicontinuous fiber is used as a counter flow reactor.

Additional embodiments of the present invention provide materials and compositions comprising bijels (bijel fibers or bijel membranes) of the present invention. Non-limiting examples of such materials and compositions include a fiber scaffold for tissue engineering (e.g., solid polymer scaffold), a cosmetic composition, a food composition, a filter, and a fog harvesting mesh. According to an additional embodiment, a cross-flow reactor may comprise bijels of the present invention. These embodiments are described in more detail below.

Porous Materials

As described by J. W. Tavacoli, J. H. J. Thijssen, P. S. Clegg, *Bicontinuous Emulsions Stabilized by Colloidal Particles*, materials with a bicontinuous structure and a bimodal pore size distribution have great potential for applications in catalysis, gas storage, and osmotic power. The idea is that combining interconnected pores at the nanometer and micrometer scales allows simultaneous optimization of active surface area and mass transport. In other words, the small pores enhance the active surface area for adsorption and heterogeneous reactions, while the large pores facilitate the rapid flow of fluid reactants or macromolecular solutions. Such materials could be obtained from bijels by using the polymerized version as a template for nanocasting, generating micropores down to about 10 nm. Such bicontinuous bimodal porous materials could also be excellent chemical sensors by using a responsive polymer either during or after the post-processing step. As demonstrated by Lee and Mohraz, a polymerized bijel can be coated with a thin layer of conductive material (e.g. copper), while retaining the softness of the polymer.

Microfluidics

As described by J. W. Tavacoli, J. H. J. Thijssen, P. S. Clegg, *Bicontinuous Emulsions Stabilized by Colloidal Particles*, in the initial publication on bijels, Stratford et al. speculated that bijels might have potential as cross-flow microreactors, in which two liquids are made to flow in opposite directions through the two separate channels, allowing intimate contact between mutually insoluble reagents. These reagents can meet at the interstices between the interfacial particles, which take up at most 90% of the liquid-liquid interface, so the particles pose a significant barrier for reagents or products only if they are of comparable size (a feature which may even be used for size selection). Notably, the set-up also purifies the reaction, as any reaction product that is soluble in either phase can be swept out continuously. This is in stark contrast to microreactor designs based on droplet emulsions, which have to run as batch processes as reagents and/or products can only be injected into/extracted from the dispersed phase by breaking the emulsion.

Fiber Scaffolds for Tissue Engineering

In the past decades, tissue engineering has emerged as a multidisciplinary field encompassing medicine, biology, and engineering in which researchers utilize various tools to fabricate tissue-like biological constructs. Such constructs should mimic the physiological environment including the structural, physical, and topographical features of the native tissues. In addition to the ultimate goal of replacing diseased and damaged organs in human body, engineered tissues can be used for diagnostic and therapeutic research. According to embodiments of the present invention, a fiber scaffold comprises a bijel of the present invention.

As an example, bijel fibers with a continuous internal water channel have great potentials to be used as fibrous scaffolds for cell growth since (i) their porous surface morphology offers many anchoring sites for cell attachment and (ii) their internal water channel combined with the porous walls could be used for the continuous supply of nutrients to promote cell growth.

Cosmetic and Food Compositions

The fibers can be utilized as novel components in skin care creams delivering essential oils or moisture to the skin. Both components can be encapsulated in the separate continuous compartments of the bijel fibers. Another cosmetic application includes haircare products, in which a dye and a bleach can be encapsulated separately but released simultaneously. Bijel fibers can contain equal phase volumes of oil and water and therefore encapsulate oil and water soluble components equally well. Moreover, since the bijel fiber has a bicontinuous structure it is stable against gravity, while droplet based cosmetics can be prone to sedimentation.

Edible bijels fibers can provide novel types of food with unusual textures or mouth feeling. Due to the bicontinuous particle stabilized nature of the fibers the texture or mechanical properties should be significantly different from emulsion droplets, a major component of mayonnaise, whipped cream or ice cream. Changing the bicontinuous domain sizes can significantly affect the mechanical properties and mouth feeling. According to particular embodiments, the bijel fibers may comprise food-grade oils (e.g., oleic acid, the major component of olive oil).

The embodiments of the invention are described above using the term "comprising" and variations thereof. However, it is the intent of the inventors that the term "comprising" may be substituted in any of the embodiments described herein with "consisting of" and "consisting essentially of" without departing from the scope of the invention. Unless specified otherwise, all values provided herein include up to and including the starting points and end points given.

The following examples further illustrate embodiments of the invention and are to be construed as illustrative and not in limitation thereof.

EXAMPLES

Example 1

As a template solution for bijel fiber formation, a monophasic ternary mixture of water, a solvent and oil is prepared. Diethylphthalate (DEP) is used for the oil since its high refractive index (1.5001) allows for high contrast light-microscopy of the phase separation process. Ethanol is selected as the solvent, but also acetic acid, DMSO or acetone can be used. The ternary liquid composition of this template solution is selected to be close to the intersection of binodal and estimated spinodal line (critical point) in the ternary phase diagram of FIG. 2A. A composition near the critical point ensures that a solvent mass transfer induced phase separation occurs through the mechanism of spinodal decomposition, generating the sponge like oil/water structures found in the fibers and films of this embodiment.

To the ternary liquid mixture, neutralized silica nanoparticles (Ludox® TMA, 22 nm diameter, pH 3) as well as the cationic surfactant cetyltrimethylammonium bromide (CTAB) are added. Particularly the CTAB addition allows for a dispersion of silica particles in the ternary mixture. It is believed that the quaternary ammonium head group of CTAB interacts with the silanol groups on the silica nanoparticles introducing hydrocarbon tails to the silica surface as depicted schematically in FIG. 2A.

The phase inversion technique takes advantage of the solubility of a polymer in a solvent, but the polymer's insolubility in a nonsolvent. In contrast, solvent and nonsolvent mix perfectly. Bringing the mixture of polymer and solvent in contact with the nonsolvent initiates the phase separation by mass transfer of the solvent.

Figure 2B:
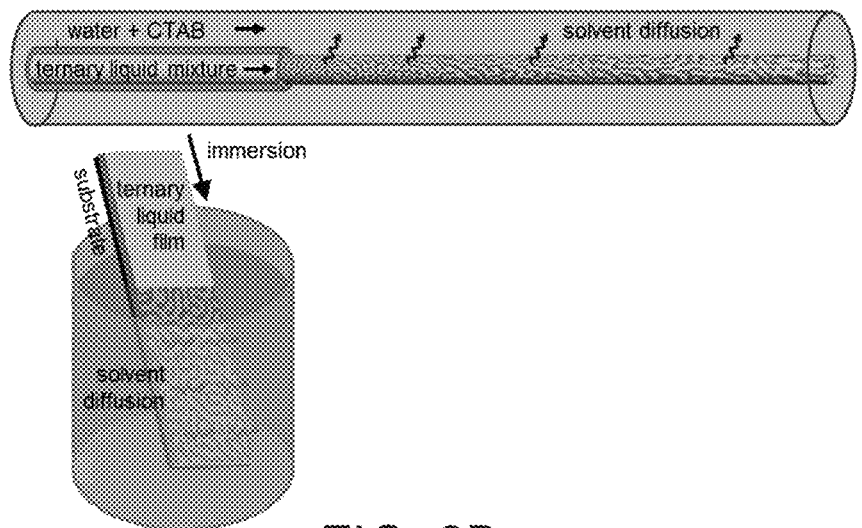
FIG. 2B provides, in accordance with embodiments of the present invention, a depiction of a microfluidic configuration for fiber formation and the experimental procedure described herein for membrane formation.

The bijel fiber or membrane formation is carried out analogously as depicted in FIG. 2B. The phase separation inducing mass-transfer reaction takes place when the ternary liquid mixture of DEP/ethanol/water is brought into contact with water. The water will absorb the ethanol and change the ternary composition. FIG. 2B depicts two ways of how this process can be initiated. The first is to jet the ternary mixture through a nozzle into a water channel. When the ternary mixture exits the outlet a spinodal phase separation is initiated, which coarsens over time and is ultimately arrested by the interfacial jamming of the nanoparticles. This method yields bijel fibers as depicted in FIG. 1A.

Glass capillary based microfluidics were used to bring the ternary liquid mixture of DEP/ethanol/water into contact with water, as follows. A segment of a square capillary (1-20 cm length, inner diameter 0.06 mm-3.5 mm) was glued horizontally onto a glass plate (wider than 0.5 cm, longer than 2 cm, thickness between 0.1 mm and 5 mm). One opening of the square capillary was located on the glass plate (left opening), the second opening reaches over the edge of the glass plate (right opening). A tapered cylindrical glass capillary (outer diameter 0.05 mm to 3 mm) was inserted with the tapered tip into the left opening of the square glass capillary. The outer diameter of the cylindrical capillary is slightly smaller than the inner diameter of the square capillary (for instance 0.02 mm smaller). The tip of the tapered capillary was moved to a distance of about 0.5 to 2 cm from the left opening of the square capillary. The opening of the cylindrical part of the round capillary was located outside of the glass plate surface. The round capillary was then glued onto the glass plate. A dispensing needle was positioned on top of the left opening of the square capillary (where the cylindrical part of round capillary sticks out). The plastic base of the dispensing needle had two small grooves at its base to allow for the fixed round and square capillary to fit in. The base of the dispensing needle was then embedded in glue (e.g. epoxy glue) to attach it to the glass plate and to seal the system. Care had to be taken to prevent any of the glue to clog the left opening of the square capillary. Two pieces pf plastic tubing were connected with the dispensing needle and the cylindrical opening of the tapered glass capillary. The tubing was connected to syringes. A syringe filled with the ternary liquid mixture was connected with the tapered cylindrical capillary. A syringe with the continuous water phase was connected to the dispensing needle. By means of two syringe pumps the ternary liquid mixture and the continuous water phase were flown into the glass capillary device. The flow rate of the continuous phase is preferably 4-20 times higher than the flow rate of the ternary liquid mixture. For example, when using a tapered capillary with 0.05 mm opening in the square capillary and a square capillary with an inner diameter of 0.3 mm the flow rate of the ternary liquid mixture could be 0.5 ml/hr and the flow rate of the water phase 4 ml/hr.

For the second, a planar substrate (here polystyrene) is coated with a thin film of the ternary liquid mixture and subsequently immersed into a water bath. The immersion initiated analogously to the fiber formation the mass transfer of ethanol from the film to the water bath, resulting in the desired spinodal phase separation, which is arrested by the interfacial jamming of nanoparticles. The resulting bijel structure is a planar membrane as depicted in FIG. 1A.

The compositional quench induced by the mass transfer for fibers or films is qualitatively depicted in the ternary phase diagram in FIG. 2A. From the miscible starting point (1) the ternary composition shifts underneath the binodal line producing a water- and a DEP-rich phase by phase separation. The exact tie-line(s) and landing point(s) (2) for this process are unknown. The process is depicted qualitatively in FIG. 2A. However, it is understood that the large excess of continuous water phase will eventually take up the entire ethanol, diluting it sufficiently to describe the final states of the process by the practically pure DEP and water phase corresponding to the lower left and right corner of the phase diagram.

Figure 2C:
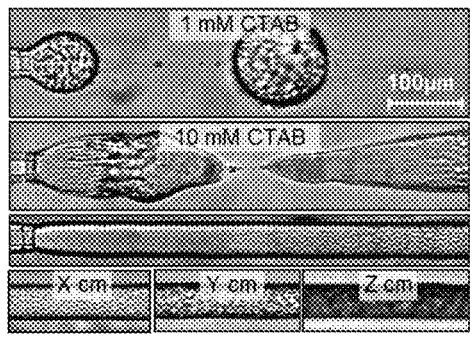
FIG. 2C provides, from top to bottom: (i) a high speed micrograph of the ternary droplet-pinch off at 1 mM CTAB concentration in the ternary mixture; (ii) a high speed micrograph of the ternary droplet-pinch off at 10 mM CTAB concentration in the ternary mixture; (iii) a micrograph of a liquid jet after capillary coating with PDADMAC at high flow rate of the ternary mixture; and (iv) micrographs of the jet at different longitudinal positions.

A high speed camera and a Hofmann contrast module on a microscope were used to capture images of the phase separation for fibers, as shown in FIG. 2C. For a CTAB concentration of 1 mM and a silica concentration of 2 wt % in the ternary mixture, droplets with dynamically evolving patterns of dark and bright contrast can be observed, indicative of the ongoing phase separation. These droplets eventually form quintuple emulsion droplets (meaning droplets with five alternating oil/water rings as described in Haase, Martin F., and Jasna Brujic. *"Tailoring of High-Order Multiple Emulsions by the Liquid-Liquid Phase Separation of Ternary Mixtures." Angewandte Chemie International Edition* 53.44 (2014): 11793-11797).

The next micrograph in FIG. 2C for 10 mM CTAB and the same silica concentration in the ternary mixture shows a completely different droplet pinch off behavior. Irregularly and elongated shaped droplets form at the capillary orifice. Also, the phase separation patterns become irregular over the volume of the droplet. The shape deformation of the droplet away from spherical suggested that at these elevated CTAB concentrations the liquid mixture becomes viscoelastic. This might be attributed to the coagulation of the silica particles.

A downside effect of the silica particle coagulation is the stickiness of the viscoelastic droplet to the glass capillary tip. The droplet pinch-off leaves a residue of aggregated material at the capillary tip behind. This causes the droplet pinch off to become irregular. After a screening of different capillary surface coatings, it was discovered that a polyelectrolyte coating comprising polydiallyldimethylammonium chloride (polyDADMAC) prevented the sticky effect. A polyDADMAC coated capillary enables the ternary liquid to flow out as a uniform jet at high ternary flow rates (FIG. 2C). Following the jet downstream allows us to observe the coarsening of the phase separation at different distances from the capillary orifice (FIG. 2C, 0.5, 1.0, 2.0 cm). At Z cm, the fiber appears dark indicating strong light scattering, and does not change its optical appearance further. The axial coarsening profile of the fiber is determined by the flow rates.

For the ternary flow rate of 250 µl/hr the fiber can be observed undulating at 2.5 cm from the capillary orifice. The distance at which the undulation starts depends on the continuous and the ternary phase flow rate. At a critical flow rate of the continuous phase the fiber gets torn off and fiber segments form (at controllable lengths).

The photograph in FIG. 2D shows the fiber exiting the microfluidic device into a collection vial. The microfluidic tubing was shortened, so that the fiber undulation starts inside the collection vial. This undulation results in the spiraling of the fiber, which then sinks to the bottom of the collection vial and accumulates there as heap of spools.

Example 2

In the following example, DEP was replaced with hexanediol diacrylate (HDA). This monomer allowed us to polymerize the fiber for SEM and confocal microscopy. HDA forms with water and ethanol a similar ternary phase diagram as DEP does. A dispersion of the silica nanoparticles is feasible with CTAB as well. When selecting a ternary composition near the critical point of the phase diagram (e.g. 42 vol-% HDA, 42 Vol-% EthOH, 16 Vol-% $H_2O$), HDA forms bijel fibers in an analogous fashion. A hydrophobic fluorescent dye (Nile red) was also introduced into the ternary mixture and the polymerized fiber was immersed in a high refractive index liquid like DEP. In this environment, the fiber became almost transparent and a clear characterization of the internal structure by confocal scanning laser microscopy (CSLM) became feasible. The fiber morphology was found to depend on several control parameters, as discussed below.

FIG. 3A shows 3D reconstructions confocal microscopy z-stacks, as well as equatorial slices of the corresponding z-stack of the fibers fabricated with different initial silica and CTAB concentrations. In this figure gray areas correspond to HDA regions of the fiber segments and white areas to water regions.

Except for the lowest silica and CTAB concentration of 4.6 wt-% and 36 mM all fibers segments show porous surface structures. For all three studied silica concentrations (columns) the surface features become finer with increasing silica concentration. Similarly, increasing the CTAB concentration for a fixed particle concentration (rows) leads to a decrease of the size of the surface features. We measure the diameter of bicontinuous surface channels and pores from the confocal micrographs and plot those numbers for different CTAB concentrations in FIG. 3B vs. the silica concentration. Here, the color code of the data points match the color of the fiber segments in FIG. 3A.

The surface pore size decreases asymptotically with increasing silica concentration to a minimum. The higher the CTAB concentration the smaller the minimum surface pore size. The smallest surface pore sizes of the polymer scaffold are approximately 400 nm. The scaffold pores may become clogged with aggregated nanoparticles and, accordingly, the effective pore diameter size may be controlled by altering silica and CTAB concentration. According to some embodiments of the present invention, pore diameter size may be controlled to a range between 10,000 nm and 5 nm. The nanoparticles are not visible in the confocal micrographs shown in FIG. 3A. However, the nanoparticles are visible in the electron micrographs shown in FIG. 6A. When aggregated nanoparticles dominate the pore size, the pore size can be reduced down to 5 nm, which is useful for ultrafiltration.

The small effective pore sizes generated by the aggregated silica particles enable ultrafiltration applications of the membranes. Alternatively, when there are no aggregated silica particles in the pores, the unpolymerized bijel scaffold is more open and applications such as liquid/liquid extraction or interfacial catalysis can become viable.

The equatorial slices besides the 3D reconstructions in FIG. 3A show the fiber interior. Beneath the porous surface layer differently shaped structures extent towards the inside. These structures have remarkably similar shapes to macrovoids found routinely in phase inversion membranes. With increasing CTAB and silica concentrations the oil structures become more frequent and finger-like. They are surrounded by water, which can be present as separated- (17.2% 36 mM, 4.6% 72 mM) or interconnected-voids (17.2% 72 mM, 9.9% 108 mM) or as a continuous channel extending through the fiber (9.9% 72 mM, 4.6%, 108 mM).

Figure 3B:
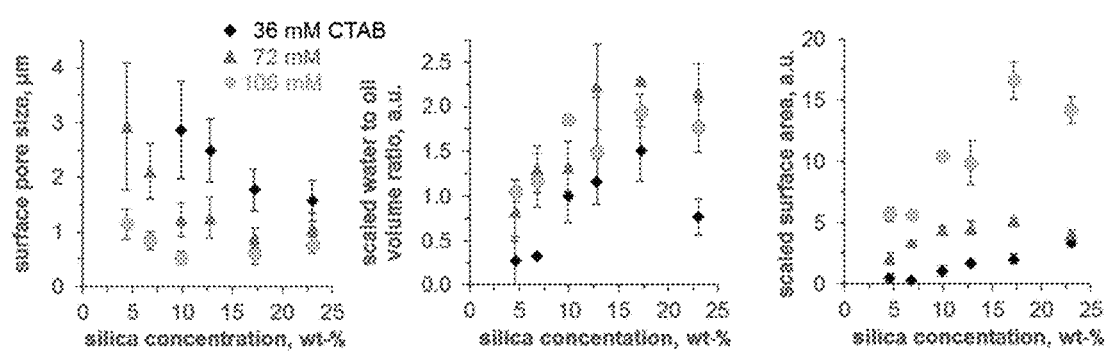

For 9.9% silica and 36 mM CTAB we measure the water to oil volume ratio of the fiber by analyzing the 3D space obtained from a confocal stack to be 1.25. For all other fibers we estimate the water to oil ratio from the 2D analysis of the equatorial slices under the assumption of axial symmetry and normalize these numbers by 1.25. FIG. 3B shows an increasing normalized water to oil ratio for an increasing silica concentration. The differences between the three investigated CTAB concentrations are less clear and lie in some cases in the error range. Interestingly the fibers contain in most cases more water than oil, which stands in contrast to the initial ternary composition with the opposite proportion.

Particularly with an increase of the CTAB concentration we can observe the occurrence of water pockets inside the internal oil structures. These start to show up for 72 mM CTAB as separated voids and turn into sponge like interconnected voids at 108 mM and 17.2%. Their presence is best reflected in surface area measurements. From the 3D analysis of the fiber segment at 9.9% and 36 mM we measure a surface area of 0.28 m2/cm3. With this as a normalization constant we plot the scaled surface area obtained from the axisymmetric 2D analysis of the equatorial slices in FIG. 3B.

The surface area increases with the silica concentration. The increase becomes steeper with increasing CTAB concentration. The increase is related to the observed decrease of surface pore sizes, increasing size of internal oil structures and the increasing number and decreasing size of pores in the oil scaffold of the fiber.

We find that the structure dependence for fibers made out of DEP differs from the dependence for HDA fibers (see FIGS. 5A, 5B). Because of the large refractive index difference between water and DEP the perspectives onto the equatorial slice of the fiber are blurry and do not reveal all details of the structure. Nevertheless, it can be observed that smaller CTAB concentrations are preferred to form structures with similar small pore sizes and internal architectures as for the HDA fibers. This indicates that the trends shown in FIG. 3A are strongly depending on the pair of immiscible liquids.

Figures 6A, 6B:
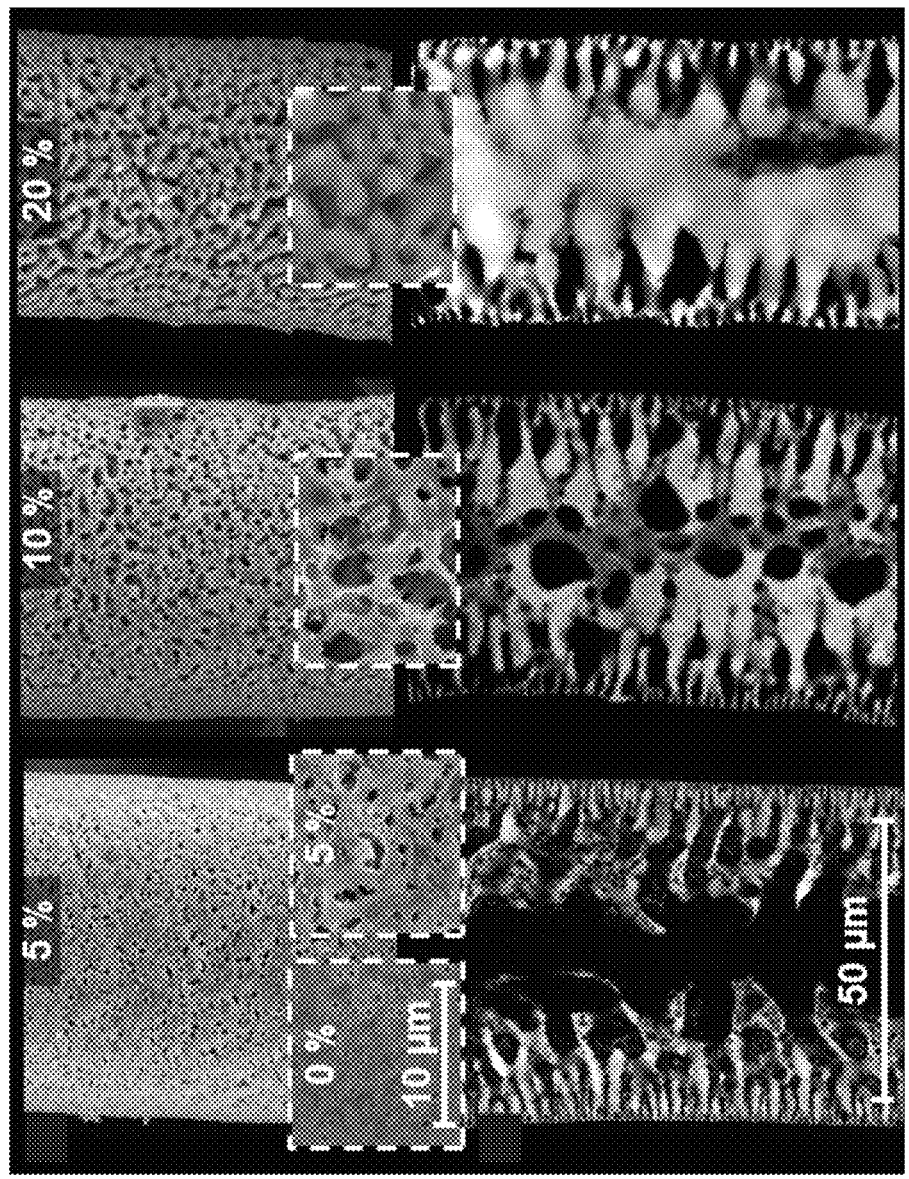
FIG. 6A provides SEM micrographs of poly(HDA) bijel fibers formed by STRIPS with varying ethanol concentrations in the continuous phase (indicated in Vol-%). Inset micrographs show magnifications of the fiber surfaces.
FIG. 6B provides CSLM micrographs of equatorial slices of the corresponding fibers. Bright areas correspond to the HDA-phase and black corresponds to the water-phase.

Initial attempts to visualize the polymerized fibers with scanning electron microscopy (SEM) revealed very different fiber surfaces than the confocal scanning laser microscopy of FIG. 3A shows. Instead of uniform pore distributions over the surface we observed nonporous surfaces with a few scattered pores of a few hundreds of nanometer in diameter. The SEM images revealed that a film of the jammed silica nanoparticles covers the fiber surface. This silica film is not visible under the confocal microscope because the fluorescent dye does not label the silica particles but only the HDA structures. FIG. 6A and FIG. 6B show how the addition of ethanol to the continuous phase can be utilized to remove the silica particle film on the fiber surface.

The effect of ethanol in the continuous phase is discussed below. FIGS. 6A and 6B show SEM micrographs of bijel fibers manufactured with 9.6 wt % silica, 33.5 mM CTAB and varying ethanol concentrations in the continuous phase. Increasing the ethanol concentration in the continuous phase (given in volume percent in the FIG. 6A) had a strong effect on the surface porosity of the bijel fiber. While the fiber surface for 0% ethanol (33.5 mM CTAB, 9.6 wt % silica) shows only a few small holes, an increase to 5% ethanol results in a significantly more porous surface structure with micrometer sized noncircular pores. At 10% and 20% ethanol, even higher surface porosities were observed. Moreover, the increase up to 20% ethanol caused the surface domains to be "more round."

The CSLM in FIG. 6B shows that alongside the increasing surface porosity the fiber transitions from hollow to a HDA filled fiber. The bottom micrographs correspond to the above SEM micrographs. White areas correspond to HAD regions, black areas to water regions. Also, the internal micropores disappear with increasing ethanol concentration.

A similar ternary composition near the critical point of the phase diagram (e.g., 41 vol-% HDA, 41 vol-% ethanol, 18% vol-% water) was prepared to form STRIPS bijel fibers. The ethanol contains 0.1 mol/l cetyltrimethylammonium bromide, the water contains an adjustable concentration of silica nanoparticles (20 nm diameter), the HDA contains 1 Vol-% 2 Hydroxy 2-methyl-1-phenyl-propan-1-one. Injecting this mixture through a nozzle into a water bath leads to the formation of a liquid bijel fiber by STRIPS. Exposing the resulting liquid fiber to UV-light (365 nm, 20 mW/cm$^2$) leads to the polymerization of the HDA, creating poly (HDA) fibers with surfaces covered by silica particles. The internal structure of the resulting fibers (shown in FIG. 4) can be tuned by changing the concentrations of silica nanoparticles and CTAB. The STRIPS bijel template hollow fiber membranes (as depicted in FIG. 4 on the right) have at least several distinct advantages compared to hollow fiber membranes fabricated by the phase inversion method:

(i) The surface of the fibers may be covered with functional nanoparticles. Besides silica particles as used for FIG. 4, many different nanoparticles can be used for STRIPS (e.g., photocatalytic TiO$_2$ particles). These particles can introduce catalytic or antifouling properties to the fiber surfaces. Introducing functional nanoparticles to phase inversion membranes succeeds only in rare cases, since it is usually not possible to disperse particles in the initial polymer solution. Moreover, once the particles can be dispersed, they are usually not on the surface of phase inversion membranes.

(ii) STRIPS bijel fibers can be fabricated out of a large variety of cross-linkable monomers. Poly(HDA) polymers, which were used to produce the fibers of FIG. 4, for instance, are highly cross-linked polymers that are very resistant to organic solvents. Thus, in comparison to most phase inversion membranes, polymerized STRIPS bijel membranes can be used as separation membranes for organic solvents and other aggressive feed liquids.

(iii) STRIPS bijel fibers can form a hollow core without the need for a bore fluid by varying the concentrations of nanoparticles (e.g., silica) and surfactant (e.g., CTAB). This simplifies the continuous production of these materials.

In summary, the liquid fibers are composed of oil stabilized by interfacially jammed silica nanoparticles in water. The solvent transfer induced phase separation (STRIPS) is the basis for this structure. The liquid fibers are highly porous, and can have either core shell or continuous structures. The surface porosity can be tuned from nonporous to highly porous. The bijel fibers may be used for various applications including bijel fiber microfluidics, interfacial heterophase catalysis, edible bijel fibers, tissue engineering bijel fibers and more.

Example 3

Figure 7A:
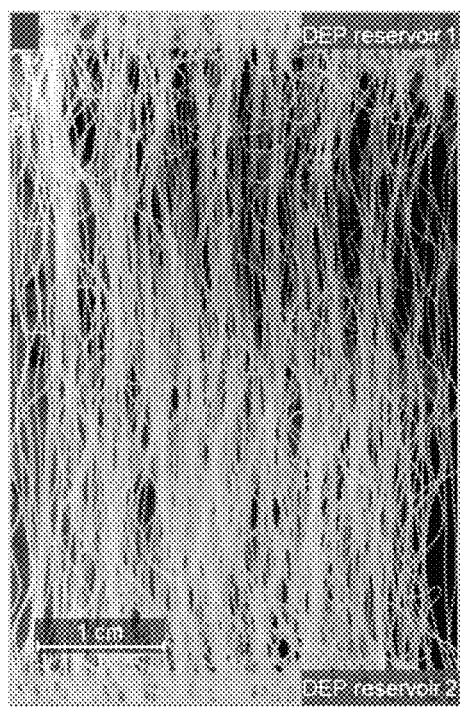
FIGS. 7A-7C provide information about fiber alignment, stability and bicontinuity, in accordance with embodiments of the present invention. All micrographs contain time information in minutes on the upper right corners.

This example demonstrates the use of liquid bijel fibers as tubes for potential microfluidic applications. FIG. 7A shows a bundle of parallel tubes as an example of aligned bijel fibers. The alignment is feasible simply by moving the outlet of the microfluidic device of FIG. 2B up and down inside a water filled petri-dish. Since here this has been done manually the alignment is imperfect.

Figure 7B:
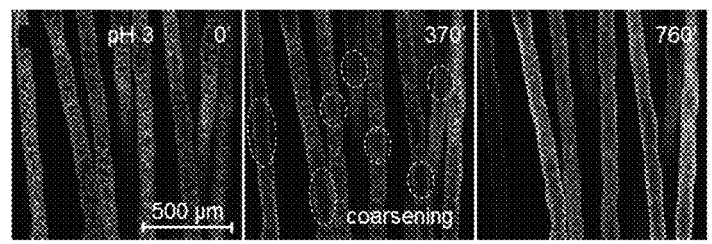

First, we study the stability of the bijel fibers by monitoring bundles of fibers over time. FIG. 7B shows a time series of eight fluorescent DEP-fibers in water at the manufacturing conditions of the continuous phase of 1 mM CTAB and pH 3. We find, that the bicontinuous domains start to coarsen after approximately 120 minutes, as highlighted by encircled regions in FIG. 7B. Interestingly, upon altering the pH value in the fiber collection bath to pH 9 no signs of coarsening can be observed after 12 hours. Also the mechanical stability of the fibers is improved by this pH increase. Without intending to be bound by any theory, it is hypothesized that the increased pH causes an enhanced silica particle aggregation due to higher adsorption densities of CTAB.

Figure 7C:
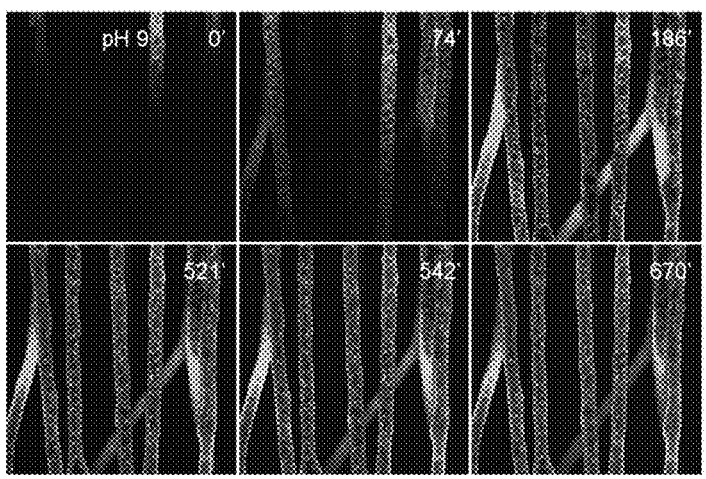

With the stability dependence in mind we now connect the fiber bundle with two DEP reservoirs as depicted in FIG. 7A at pH 9. For this experiment, the fibers have not been labelled fluorescently, but the DEP in the reservoirs contains the fluorescent dye. FIG. 7C shows how the fluorescent dye diffuses throughout the fibers with time. After 3 hours the entire DEP space of the fibers in this section has become colored by the dye. We leave the system undisturbed for six more hours during which we see no signs of coarsening. Then we inject the hydrophilic fluorescent dye fluorescein into the water phase and observe initially the staining of the fiber surface (542 min) and after 640 min the diffusion of the dye towards the internal regions of the fibers. The intense blue coloring around the contours of the bicontinuous domains indicates an accumulation of fluorescein on the surface of the aggregated silica particles.

According to particular embodiments, the bijel fibers are usable as microfluidic tubes with manifold potential applications. For example, hydrogel based walls formed by photolithography may be used to compartmentalize sections of the fibers into different chambers. Connecting these chambers with in- and outlets allow us to flow oil through and water around the fibers. This construct may serve as a continuously operated mass-transfer apparatus for a solute travelling across the oil water interface.

Example 4

It is possible to tune the surface porosity of these fibers in-situ, by fabricating swellable hydrogel fibers. Swelling causes pore opening, and shrinking causes pore closing. In this example bijel fibers were transformed into pH sensitive porous polyacrylic acid hydrogel fibers. As depicted in FIG. 8B, fibers are fabricated with a polymerizable monomer (e.g., tertiary butylacrylate) and small amounts of a cross-linker (e.g., HDA). Then, after polymerization, cross-linked poly(tert-butylacrylate) fibers are formed. This polymer can be converted to the hydrogel polyacrylic acid upon hydrolysis. Polyacrylic acid is a pH responsive polymer and can be swollen/shrunken upon changing the pH.

Figure 8A:
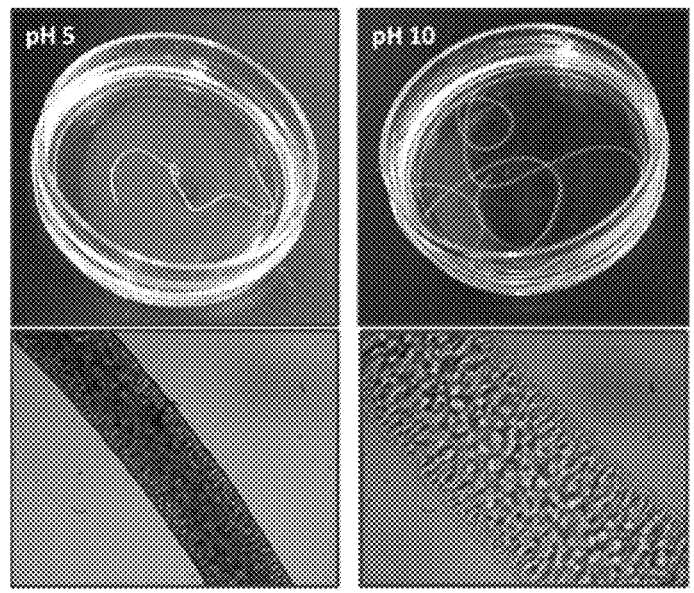
FIG. 8A depicts photographs and micrographs of resulting poly(acrylic acid) (PAA) bijel fibers for two different pH values.
Figure 8B:
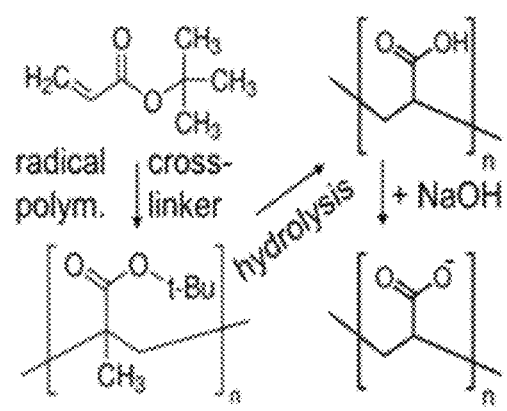
FIG. 8B depicts the chemical pathway for the reaction of tert-butyl acrylate to poly(tert butylacrylate) upon radical polymerization, and the subsequent hydrolysis of the poly (tert-butylacrylate) to polyacrylic acid.

The bijel fibers depicted in FIG. 8A were first formed with a ternary mixture of tert-butylacrylate (40 vol-%), ethanol (40 vol-%), water (20 vol-%), Ludox particles (9.9 wt-%), CTAB (36 mM) and 2-hydroxy-2-methylpropiophenone (0.1 wt-%). The resulting bijel fibers were polymerized upon UV light radiation. After the polymerization the fibers were introduced into a mixture of 20 Vol-% formic acid in trifluoroacetic acid and left at room temperature overnight. Then the fibers were washed in ethanol several times and transferred into water.

FIG. 8A shows photographs of the resulting polyacrylic acid hydrogel fibers (diameter here approximately 20 micrometer at pH 5). Adding sodium hydroxide to alter the pH value to 9 causes a drastic swelling of the fibers due to deprotonation of the acrylic acid groups (which is illustrated in FIG. 8B). The change in diameter is visible with the naked eye (photographs FIG. 8A) as well as under the light microscope (micrographs FIG. 8A). The swelling causes the surface pores of the fibers to expand.

Such hydrogel fibers/membranes may serve for stimuli responsive separation processes. For instance, at alkaline pH values the pores are widely open and allow suspended materials to pass through the membrane. At acidic pH values the surface pores decrease in size and prevent the suspended materials to pass through the membrane. The results demonstrated here for the bijel fibers are analogously valid for the bijel membranes. In addition to pH-dependent expansion and shrinkage, the degree of swelling by polymerized fibers can be controlled by the concentration of cross-linker (e.g., HDA).

Example 5

With the microfluidic device employed in the examples it is possible to fabricate bijel fibers of specified lengths. The length of the fibers can be controlled by the continuous water and ternary flow rates. In the following example we utilized a round capillary of 50 micrometer inner diameter, centered in a second round capillary of 300 micrometer diameter. The ternary mixture was then extruded through the smaller capillary at the specified "ternary flow rate" in μl/hr into the larger capillary at the specified "water flow rate" in ml/hr. FIG. 9A shows snapshot micrographs of fiber segments just after pinch-off during their flow towards the right side of the picture for a constant ternary flow rate of 50 μl/hr. Left to these snapshots the water flow rate is indicated in ml/hr. It can be seen that an increase of the water flow rate causes the fiber segments to become shorter. The reason for this effect to occur is the increased shear stress experienced by the fiber for increased water flow rate.

The diagram in FIG. 9B shows the preferred water and ternary flow rates to fabricate fibers of the average lengths: 0.4 mm+/−0.02 mm, 0.8 mm+/−0.05 mm, 2 mm+/−0.5 mm, 5 mm+/−1 mm. The uppermost curve indicates the boundary at which the transition to continuous fibers takes place.

Example 6

In this example, planar bijel membranes were formed using the same ingredients. Instead of flowing the nanoparticle and surfactant doped ternary liquid mixture into a water channel, a flat substrate was coated with a thin film of the liquid mixture and subsequently immersed into a water bath (FIG. 2B). By the same mechanism of ethanol mass transfer to the water bath, a spinodal phase separation was initiated in the film (STRIPS process). The surfactant modified nanoparticles then arrested the phase separation to obtain a planar porous film on the substrate.

FIG. 1A shows a 3-dimensional section of the resulting bijel film visualized by confocal scanning laser microscopy. In this micrograph, the dark areas correspond to oil and the bright areas to water. The top surface of the film comprised a thin layer of pores with sizes in the micrometer and sub-micrometer range (see inset). Below the surface, vertically aligned cavities extend downwards. It is possible to tune the size of the surface pores and the architecture of the underlying scaffold by adjusting the surfactant and nanoparticle concentrations, the ternary liquid composition, the type of oil, the composition of the continuous water bath and the introduction of additives.

By using a monomer such as 1,6-hexanedioldiacrylate as the oil in the ternary mixture, the film can be polymerized to obtain a porous solid film. It is then possible to utilize the film as a membrane for size selective separation processes. For example, the membrane can be used for water disinfection by removing bacteria or virus particles, for juice clarification in the food industry or other filtration applications. Also, in its liquid form the film has potentials for applications of extraction or interfacial catalysis as described above for the bijel fibers.

Figure 10A:
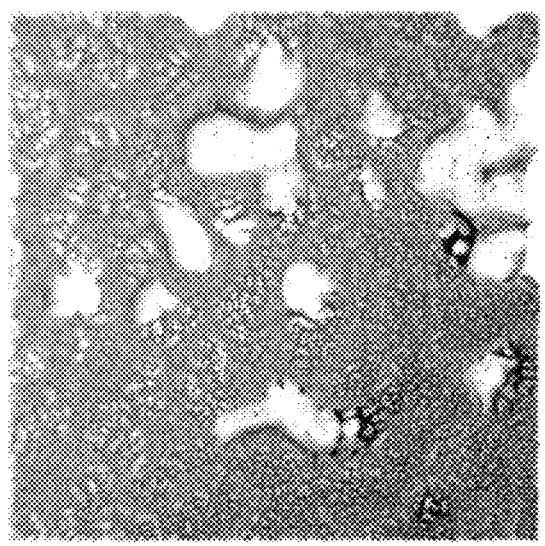
FIGS. 10A and 10B provide top views of embodiments of bijel membranes formed by STRIPS (confocal scanning laser micrograph reconstructions).
Figure 10B:
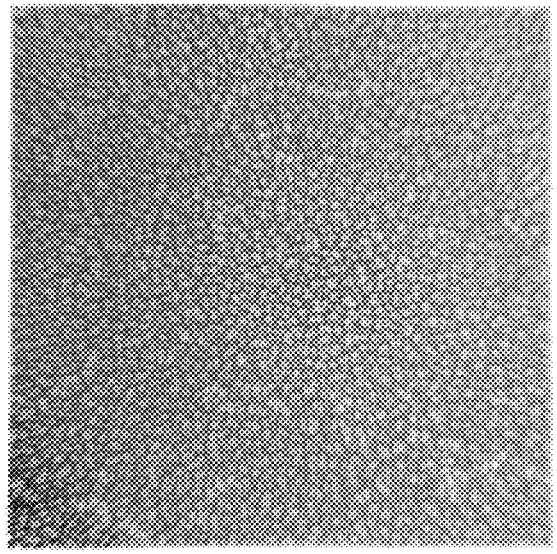

To obtain a uniform film, the selection of the supporting substrate plays an important role. FIG. 10A shows a top view section of a film obtained on a glass substrate. FIG. 10B shows a top view section of a bijel film obtained on a polystyrene substrate. The film formed on a glass substrate was interspersed with holes, while on a polystyrene substrate a uniform membrane was obtained. The uniformity of the film depends on the substrate material because of wetting conditions. It is preferred that the substrate is wetted by the ternary liquid mixture to form a uniform liquid film prior to the STRIPS process. In this example, the ternary liquid mixture of 1,6-hexanedioldiacrylate, ethanol and water wets the polystyrene, but not the glass surface.

Example 7

In this example, the separation selectivity and flux properties of silica stabilized poly(HDA) fibers is tested. First, STRIPS bijel fibers are reliably collected as aligned bundles by means of a water filled collection container (FIG. 11A). With a single extrusion nozzle, this device can currently fabricate bijel fibers at a rate of 150 meters per hour (higher rates possible).

After polymerization, these straight fibers are assembled into a separation membrane testing devices (FIG. 11B).

Partially embedded in epoxy glue, the fibers are sandwiched between two glass plates. Steel needles for in and outlets are integrated. Plastic tubing is connected to a pressurized liquid reservoir for testing the flux through the membrane wall of the hollow fibers at constant pressure.

Figure 12A:
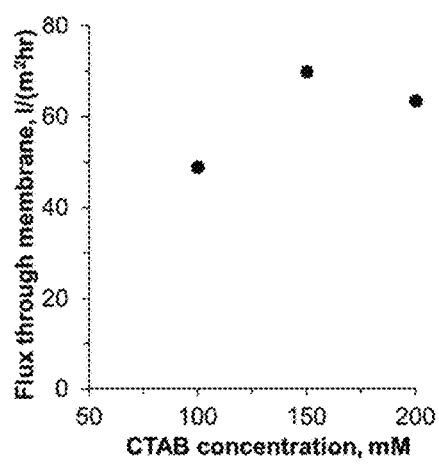
FIG. 12A illustrates flux dependence of silica-stabilized poly(HDA) bijel fibers on the CTAB concentration within the ternary liquid mixture at a constant silica concentration. The flux was maintained at a constant pressure of 1 bar (15 psi).
Figure 12B:
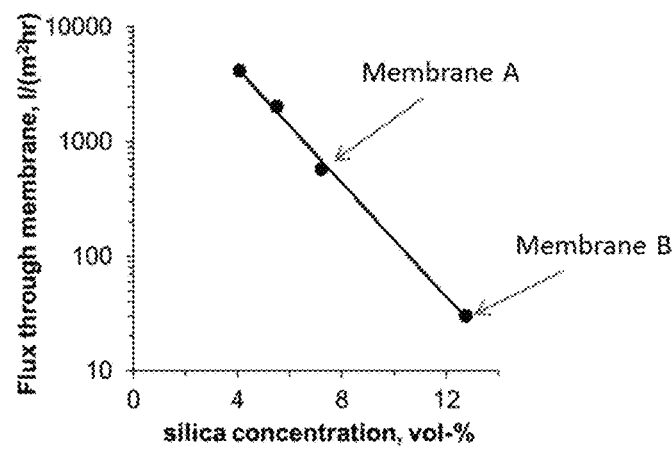
FIG. 12B illustrates flux dependence of the silica-stabilized poly(HDA) bijel fibers on the silica particle concentration within the ternary liquid mixture. The flux was maintained at a constant pressure of 1 bar (15 psi) and a constant CTAB concentration.

The flux was measured through the membranes at a constant pressure of 1 bar. Varying the CTAB concentration at a constant silica concentration did not significantly change the flux (FIG. 12A). However, a strong dependence of the flux upon the silica particle concentration was found (FIG. 12B). The flux can be changed by three orders of magnitude from 4,224 l/(m²hr) to 30.4 l/(m²hr) by changing the silica concentration in the initial ternary mixture from 4 vol-% to 12.7 vol-%, respectively.

With reference to FIG. 12B, the flux for a fiber membrane prepared with 7.2 vol-% silica particles (Membrane A, 580l/(m²hr)) is comparable to a typical PVDF microfiltration membrane. On the other hand, the flux for a fiber membrane prepared with 12.7 vol-% silica particles (Membrane B, 30l/(m²hr)) is comparable to an ultrafiltration membrane (e.g. Pebax 1074 PVDF, 50l/(m²hr)).

The flux properties of Membranes A and B were further tested by carrying out a dead end filtration with gold nanoparticle suspensions using the membrane testing devices of FIG. 11B. Two batches of gold nanoparticles were synthesized by citric acid reduction of gold chloride. Two different batches of monodisperse gold nanoparticles with diameters of 100 nm and 15 nm, respectively, were synthesized (virus particles have sizes between 5 nm-300 nm). The suspensions were both pushed from the outside towards the inside of the hollow fiber membranes (feed chamber in separation membrane testing device, see FIG. 11B and FIGS. 12A and 12B) at a constant pressure of 1 bar. The resulting filtrate liquid was then characterized by means of visual inspection and UV-vis spectroscopy (FIGS. 13A and 13B).

FIG. 13A displays the UV-vis spectra and photographs resulting from the aqueous dispersion of 100 nm gold particles fluxed through Membrane A having 7.2 vol-% silica particles. FIG. 13B displays the corresponding UV-vis spectra and photographs resulting from the aqueous dispersion of 15 nm gold particles fluxed through Membrane B having 12.7 vol-% silica particles. When flowing the 100 nm particle suspension through membrane A, the filtrate still contains gold nanoparticles (as can be visually detected in the photograph of FIG. 13A). However, the UV-vis spectra of FIG. 13A shows a decrease of the characteristic peak, indicating a partial retention of the 100 nm gold particles by the membrane. With reference to FIG. 13A, both UV-vis spectra and photographs of feed and filtrate demonstrate that full separation could not be achieved by Membrane A.

Figure 14:
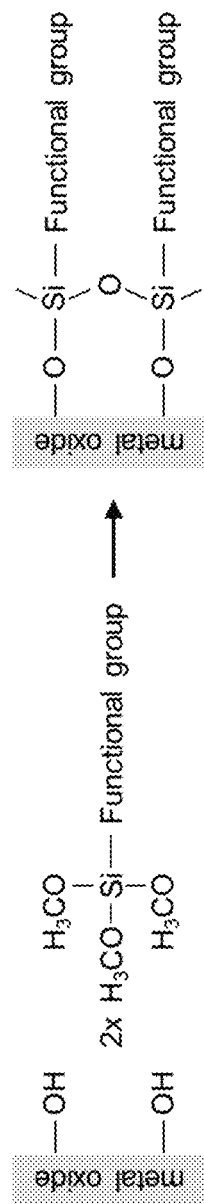
FIG. 14 depicts a schematic of surface modification of membranes by silanization.

In contrast, flowing the 15 nm particle suspension through Membrane B yields a transparent filtrate (demonstrated in the photograph of FIG. 14). The UV-vis spectra of FIG. 13B shows a complete disappearance of the characteristic peak, indicating complete removal of the gold particles by Membrane B. This experiment demonstrates the successful implementation of STRIPS bijel membranes for ultrafiltration applications. With reference to FIG. 13B, both UV-vis spectra and photographs of feed and filtrate demonstrate that full separation could be achieved by Membrane B.

Example 8

After polymerization of the oil or water phase of the membranes a variety of surface modifications of the nanoparticle covered membranes can be easily realized. These surface modifications can introduce functional groups to the membrane surface that can prevent membrane-fouling, introduce catalytic activity for chemical reactions on the membrane surface, or transform the membrane surface wettability for oil/water emulsion separation. A well-established method to chemically link functional groups to metal oxide surfaces is silanization (FIG. 14).

Figure 15A:
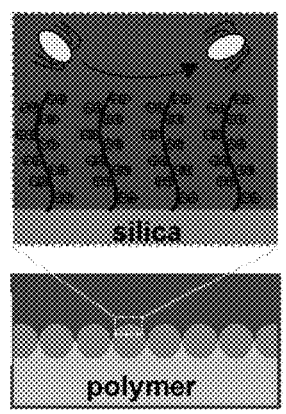
FIG. 15A illustrates surface modifications of membranes having a silica surface.

Typically, this reaction is catalyzed by acetic acid in a water/ethanol mixture. In the present case the metal oxide nanoparticle coverage of the membrane surface facilitates this approach. Non-limiting examples of functional groups are zwitterionic polymers (anti-fouling, see FIG. 15A), sulfates (catalytic), alkyl-chains, fluorocarbons or polyethylene glycols (oil/water separation).

Figure 15B:
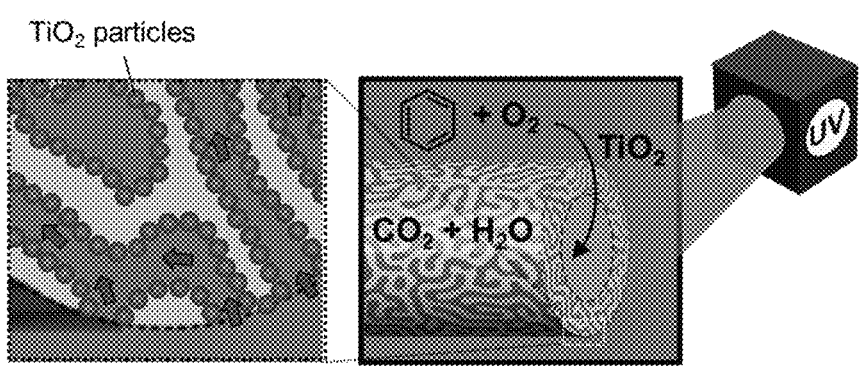
FIG. 15B illustrates a schematic of polymeric bijel fibers and membranes produced using $TiO_2$ nanoparticles in place of silica nanoparticles.

An alternative strategy to introduce functionalities to the membrane surface is to use functional particles directly for the membrane fabrication. For instance, $TiO_2$ nanoparticles have successfully been used to fabricate polymeric bijel fibers and membranes similar to the silica bijel fibers and membranes. A different surfactant, the anionic surfactant docusate sodium salt, was used in combination with titania nanoparticles at pH 2 to result in bijels stabilized by the interfacial jamming of $TiO_2$ particles as schematically represented in FIG. 15B. Appropriate surfactants for use in constructing bijels using different nanoparticles will be known to those of skill in the art. Besides functioning as separation membranes, these $TiO_2$ membranes will also facilitate the photocatalytic oxidation of organic contaminants in water (FIG. 15B).

Experimental Methods

The ternary liquid mixture was prepared from the following constituents: (i) pure ethanol, (ii) a solution of 200 mM cetyltrimethylammonium bromide (CTAB) in ethanol, (iii) a suspension of Ludox TMA in water at pH 3, (iv) pure water, and oil (in these examples, hexanedioldiacrylate, butylacrylate or diethylphthalate (DEP)).

The Ludox TMA suspension was purchased from Sigma Aldrich with a silica concentration of 33 wt-% and a pH value between 5-7. Upon adding 1 mol/l hydrochloric acid, the suspension was titrated to pH 3. This suspension is usually concentrated by partial evaporation of water and a subsequent dialysis to lower the ionic strength. This however is not essential since bijel fibers can already be obtained with the titrated original Ludox TMA suspension.

The CTAB powder (BioUltra >99%), hexanedioldiacrylate (technical grade, 80%), diethylphthalate (99.5%) were purchased from Sigma Aldrich and used without further purification. Pure water and pure ethanol 200 proof (>99.5%) was used for all the experiments.

To exemplify the preparation of 5 milliliter of a typical ternary mixture to form a polymer fiber, a concentration of 70.5 mM CTAB, 6.8 wt-% silica, 0.42 wt-% 2-hydroxy-2-methylpropiophenone, and a ternary composition of 41.7 Vol-% hexanedioldiacrylate, 41.7 Vol-% ethanol solution and 16.6 Vol-% aqueous phase was selected. Added to this was 2.06 ml hexanedioldiacrylate, 0.42 ml of pure ethanol, 1.67 ml of the 200 mM CTAB in ethanol solution, 0.021 ml of 2-hydroxy-2-methylpropiophenone, 0.755 ml of the 33 wt-% Ludox TMA suspension and 0.075 ml of water. Simple shaking of this mixture is typically enough to produce a clear liquid with well dispersed silica nanoparticles (for lower CTAB concentrations sonication may be necessary).

The continuous aqueous phase for the fiber formation has a concentration of 1 mM CTAB and is titrated to pH 3.

The distance between the tip of the fiber extrusion capillary and the end of the outer capillary can be varied between a few millimeters up to several centimeters. The opening of the outer capillary is immersed into a bath of the continuous phase. In FIG. 3A a 7 centimeter tall and 2 centimeter wide glass vial was used. By extruding the fiber into a shallow petri dish either the movement of the petri dish itself, or the movement of the class-capillary outlet enable the alignment of the fiber (FIG. 3B).

To produce bijel fiber templated polymer fibers, a monomer as the oil in the ternary mixture was used. This can for instance be butylacrylate, 1,6-hexanedioldiacrylate, 1,6-butanedioldiacrylate, or many others. A small amount of a radical initiator (typically 0.1-1.0 wt-% of the monomer mass) is added to initiate the polymerization. This can be for instance azobisisobutyronitrile (AIBN) or 2-hydroxy-2-methylpropiophenone (Darocur 1173). To initiate the polymerization with AIBN heat is used (70° C.), while for Darocur 1173 UV-light (<320 nm) is used. Also, 1 wt-% Darocur 1173 can be added to the 1,6 hexanedioldiacrylate fraction of the ternary mixture, and the fiber can be polymerized after complete phase separation with UV-light. Therefore, the fiber is flown into a water filled cylindrical container (height 7 cm) from the top to accumulate at the bottom of the container. The resulting fiber pile is then exposed to high intensity UV light (20 W/m2) for 3 minutes.

The ternary liquid mixture used for the films shown in FIGS. 1 and 10 included 41.7 Vol-% 1,6-hexanedioldiacrylate, 41.7 Vol-% ethanol and 16.6 Vol-% water. The water constituent of the ternary mixture contained 44.2 wt % Ludox® TMA particles (pH 3), the ethanol constituent 240 mM cetyltrimethylammonium bromide. The 1,6-hexanedioldiacrylate constituent contained 0.1 wt % 2-Hydroxy-2-methyl-1-phenyl-propan-1-one (photoinitiator) and 0.01 wt % Nile red (fluorescent dye).

A planar 0.5 mm thick polystyrene plate was immersed for 5 seconds into the ternary liquid mixture. The plate was taken out by means of a pair of tweezers and subsequently immersed into a water bath containing 1 mM CTAB at pH 3. More uniform films can be obtained by utilizing different film formation techniques such as spin coating or the application of a coating knife.

After 1 minute, while still immersed in the water bath, UV-light (340 nm) at an intensity of 10 mW/cm$^2$ for 20 seconds was shone onto the film. The film was then washed with ethanol and dried. For the visualization under the confocal microscope, a droplet of diethylphthalate (refractive index matching fluid) was added onto the film and a laser wavelength of 490 nm was used to visualize the structure of the film.

The embodiments described herein are intended to be exemplary of the invention and not limitations thereof. One skilled in the art will appreciate that modifications to the embodiments and examples of the present disclosure may be made without departing from the scope of the present disclosure.

What is claimed:

1. A bicontinuous interfacially jammed emulsion that is a bijel having temperature-independent stability, the bijel made according to:
    dispersing surface-active nanoparticles into a monophasic ternary liquid mixture to give rise to a loaded mixture, a surface-active nanoparticle having a water-soluble ionic surfactant associated thereon,
        wherein the monophasic ternary liquid mixture comprises a hydrophilic liquid, a hydrophobic liquid, and a solvent,
        wherein the hydrophilic liquid comprises (i) a liquid that comprises at least one of water, ethylene glycol, and ethane diol, (ii) a polymerizable monomer, or (iii) a combination of the liquid and the polymerizable monomer,
        wherein the hydrophobic liquid comprises (i) a liquid that comprises at least one of diethyl phthalate, dimethylphthalate, 1,6-hexanediol diacrylate, 1,6-diacetoxyhexane, trimethylolpropane triacrylate, dipentaerythritol pentaacrylate, triacetin, toluene, chloroform, laurylacrylate, butylacrylate, decanol, styrene, and oleic acid, (ii) a polymerizable monomer, or (iii) a combination of the liquid and the polymerizable monomer,
        wherein the solvent comprises at least one of ethanol, acetic acid, methanol, propanol, tetrahydrofuran, dimethyl sulfoxide (DMSO), or acetone, and
        wherein the surface-active nanoparticles are equally wettable by both the hydrophilic liquid and the hydrophobic liquid; and
    contacting the loaded mixture with water so as to initiate phase separation through spinodal decomposition and induce mass transfer of the solvent and give rise to the bijel.

2. A fiber scaffold for tissue engineering, comprising the bijel of claim 1.

3. A cosmetic composition, comprising the bijel of claim 1.

4. A food composition, comprising the bijel of claim 1.

5. A filter comprising the bijel of claim 1.

6. A fog harvesting mesh comprising the bijel of claim 1.

7. A cross-flow reactor comprising the bijel of claim 1.

8. A bicontinuous interfacially jammed emulsion that is a bijel, comprising:
    a stable mixture of two immiscible liquids separated by an interfacial layer of colloidal surface-active nanoparticles equally wettable by the two immiscible liquids, a surface-active nanoparticle of the interfacial layer of colloidal surface-active nanoparticles having a water-soluble ionic surfactant associated thereon,
    wherein one of the two immiscible liquids is a hydrophilic liquid and the other of the two immiscible liquids is a hydrophobic liquid,
    wherein the hydrophilic liquid comprises (i) a liquid that comprises at least one of water, ethylene glycol, and ethane diol, (ii) a polymerizable monomer, or (iii) a combination of the liquid and the polymerizable monomer,
    wherein the hydrophobic liquid comprises (i) a liquid that comprises at least one of diethyl phthalate (DEP), dimethylphthalate, 1,6-hexanediol diacrylate, 1,6-diacetoxyhexane, trimethylolpropane triacrylate, dipentaerythritol pentaacrylate, triacetin, toluene, chloroform, laurylacrylate, butylacrylate, decanol, styrene, and oleic acid, (ii) a polymerizable monomer, or (iii) a combination of the liquid and the polymerizable monomer,
    wherein the bijel has temperature-independent stability, and
    wherein the bijel has domain sizes of below one micrometer.

9. The bijel of claim 8, wherein the bijel is a bijel fiber or a bijel membrane.

10. The bijel of claim 8, wherein the hydrophobic liquid comprises hydrophobic polymerizable monomers, the hydrophobic polymerizable monomers comprising at least one of 1,6-hexanediol diacrylate, butylacrylate, laurylacrylate, styrene, trimethylolpropane triacrylate, or dipentaerythritol pentaacrylate.

11. The bijel of claim 8, wherein at least one of the hydrophilic liquid and the hydrophobic liquid comprises the polymerizable monomer.

12. The bijel of claim 8, wherein the domain sizes are between 1 micrometer and 300 nm.

13. The bijel of claim 8, wherein the domain sizes are between 1 micrometer and 500 nm.

14. The bijel of claim 8, wherein the hydrophobic liquid comprises diethyl phthalate, dimethylphthalate, 1,6-hexanediol diacrylate, 1,6-diacetoxyhexane, trimethylolpropane triacrylate, dipentaerythritol pentaacrylate, laurylacrylate, butylacrylate, oleic acid, chloroform, styrene, triacetin, decanol, or toluene.

15. The bijel of claim 8, wherein the hydrophilic liquid is water.

16. The bijel of claim 8, wherein the bijel further comprises a solvent selected from at least one of ethanol, acetic acid, methanol, propanol, tetrahydrofuran, dimethyl sulfoxide (DMSO) or acetone.

17. The bijel of claim 16, wherein the solvent comprises ethanol, methanol, or propanol.

18. The bijel of claim 8, wherein the bijel is in the form of a fiber.

19. The bijel of claim 8, wherein the bijel is in the form of a membrane.

* * * * *

UNITED STATES PATENT AND TRADEMARK OFFICE
CERTIFICATE OF CORRECTION

| | | |
|---|---|---|
| PATENT NO. | : 12,351,712 B2 | Page 1 of 1 |
| APPLICATION NO. | : 17/534500 | |
| DATED | : July 8, 2025 | |
| INVENTOR(S) | : Martin F Haase et al. | |

It is certified that error appears in the above-identified patent and that said Letters Patent is hereby corrected as shown below:

In the Specification

Under Column no. 17, Line no. 40, Replace:
"mol/1"
With:
--mol/l--

Under Column no. 21, Line no. 17, Replace:
"580l/($m^2$hr))"
With:
--580 l/($m^2$hr))--

Under Column no. 21, Line no. 20, Replace:
"30l/($m^2$hr))"
With:
--30 l/($m^2$hr))--

Under Column no. 21, Line no. 21, Replace:
"50l/($m^2$hr))"
With:
--50 l/($m^2$hr))--

Signed and Sealed this
Nineteenth Day of August, 2025

Coke Morgan Stewart
*Acting Director of the United States Patent and Trademark Office*